US006707553B1

(12) United States Patent
Imura

(10) Patent No.: US 6,707,553 B1
(45) Date of Patent: Mar. 16, 2004

(54) COLOR MEASURING APPARATUS

(75) Inventor: Kenji Imura, Toyohashi (JP)

(73) Assignee: Minolta Co., Ltd., Osaka (JP)

( * ) Notice: Subject to any disclaimer, the term of this patent is extended or adjusted under 35 U.S.C. 154(b) by 571 days.

(21) Appl. No.: 09/634,992

(22) Filed: Aug. 8, 2000

(30) Foreign Application Priority Data

Aug. 10, 1999  (JP) .......................................... 11-226174

(51) Int. Cl.[7] .................................................. G01J 3/46
(52) U.S. Cl. ...................................... 356/402; 356/425
(58) Field of Search ................................ 356/402–407, 356/425; 359/227; 396/563

(56) References Cited

U.S. PATENT DOCUMENTS

| | | | | |
|---|---|---|---|---|
| 4,479,718 A | * | 10/1984 | Alman | 356/405 |
| 4,917,495 A | * | 4/1990 | Steenhoek | 356/328 |
| 5,151,751 A | * | 9/1992 | Nakajima et al. | 356/402 |
| 5,477,438 A | * | 12/1995 | Nakata et al. | 362/259 |
| 5,583,642 A | * | 12/1996 | Nakazono | 356/405 |
| 5,592,294 A |   | 1/1997 | Ota et al. | 356/402 |
| 5,706,083 A | * | 1/1998 | Iida et al. | 356/328 |
| 5,963,334 A | * | 10/1999 | Yamaguchi et al. | 356/425 |

* cited by examiner

*Primary Examiner*—Russell Adams
*Assistant Examiner*—Michelle Nguyen
(74) *Attorney, Agent, or Firm*—McDermott, Will & Emery

(57) ABSTRACT

A measurement controller is electrically connected with light emitting circuits and controls the light emission of light sources. A calculator calculates reflection characteristic measurement values of a measurement object corresponding to the respective illuminators. Undetermined coefficients of a Gaussian function stored in a memory are determined using the calculated reflection characteristic measurement values, and errors created by an angle of inclination of a normal to a surface of the measurement object with respect to a center axis of a main body are corrected using the Gaussian function whose undetermined coefficients are determined to obtain corrected reflection characteristic values. Since a measurement result is corrected according to the angle of inclination of the main body with respect to the object surface, this enables a high-precision colormetry.

28 Claims, 13 Drawing Sheets

COLOR MEASURING APPARATUS

This application is based on patent application No. 11-226174 filed in Japan, the contents of which are hereby incorporated by references.

BACKGROUND OF THE INVENTION

This invention relates to a measuring apparatus for measuring a characteristic of an object, and particularly to an apparatus for measuring a color of a metallic coating and a pearl-color coating.

In a metallic coating and a pearl-color coating used as a coating of an automotive vehicle, bright materials 101 comprised of thin pieces of aluminum or mica is contained in a film 102 as shown in FIG. 13. Since the orientation of the bright materials 101 varies as shown in FIG. 13, the intensity of light reflected by the bright materials 101 differs depending upon a viewing direction, which provides a metallic effect and a pearl effect. Multi-angle calorimeters of the type in which illumination light is projected in one direction and detected in a multitude of directions or illumination light is projected in a multitude of directions and detected in one direction are used as calorimeters for measuring the color of the metallic coating and the pearl-color coating having such a characteristic.

Conventionally, multi-angle calorimeters whose light detecting direction is mechanically changed include those of the type in which an illumination light is projected in one direction and detected in a multitude of directions, but those of the type in which illumination lights are projected in a multitude of directions and detected in one direction are widely used as portable multi-angle calorimeters used on the spot since they have a high reliability because not having a movable portion and have a shorter measurement time.

A known multi-angle calorimeter of the type in which illumination light is projected in a multitude of directions and detected in one direction is provided with a light detector 104 for detecting reflected right in a direction at 45° to a normal to a surface of a measurement object 103 and three illuminator 106, 107 for illuminating the measurement object 103 in three directions as shown in FIG. 14. In such a multi-angle calorimeter, illuminating directions by the respective illuminators are generally based on a regular reflection direction of the light detecting direction, i.e., a direction (S in FIG. 14) symmetrical with the light detecting direction with respect to the normal to the object surface and expressed by angles with a side where the normal to the object surface is located being positive. One illuminating direction is set, for example, at 45°, i.e., the normal direction (center axis of a calorimeter main body) to the object surface (illuminator 106), the second illuminating direction is set, for example, at 15° closer to the regular reflection direction of the light detecting direction (illuminator 105), and the last illuminating direction is set, for example, at 110° closer to the light detecting direction (illuminator 107). Lights reflected by the measurement object 103 when the measurement object 103 is illuminated in the respective illuminating directions are detected by the light detector 104, and a reflection characteristic and a color value are obtained based on an amount of the detected light, and characteristics of the measurement object are expressed by the reflection characteristic and the color value in the respective illuminating directions. Generally, illuminating directions closer to the regular reflection direction of the light detecting direction are referred to as highlight directions, whereas those closer to the light detecting direction are referred to as shade directions.

The bright materials 101 shown in FIG. 13 are so arranged as to be substantially parallel to an outer surface of the film 102 (a normal 101$in$ to the bright materials 101 and a normal 102$n$ to the outer surface of the film 102 are substantially parallel to each other). If an angle between the normal 101$n$ and the normal 102$n$ is assumed to be t as shown in FIG. 13, an angle distribution P(t) displays a characteristic approximate to a normal distribution having a peak at t=0 as shown in FIG. 15. Accordingly, an angle distribution of the reflected light from the bright materials when a metallic coating or a pearl-color coating is illuminated in a certain direction also approximates to a normal distribution having a peak in a regular reflection direction (i.e., direction symmetrical with the illuminating direction with respect to a normal to the film surface) by the film surface.

When a reflection characteristic R(x) is measured by illuminating the measurement object in various directions, it contains components by diffused reflected light $L_d$ having no angle dependency and those by regularly reflected light from the surface of the measurement object in addition to those by the reflected light from the bright materials. In the illumination in the shade direction distant from the regular reflection direction of the light detecting direction, there is almost no contribution of the reflected light from the bright materials, and the reflection characteristic moderately changes upon a change in the angle of the illuminating direction. On the other hand, in the illumination in the highlight direction close to the regular reflection direction of the light detecting direction, there is a significantly large contribution of the reflected light from the bright materials since the reflection surfaces of the bright materials are mostly substantially parallel to the object surface as shown in FIG. 15, and the reflection characteristic steeply changes upon a change in the angle of the illuminating direction. In the illumination in the direction at 45° to the light detecting direction, the reflection characteristic displays an intermediate characteristic between the above two cases.

Since the reflection characteristic by the illumination in the highlight direction is particularly essential in understanding the property of the bright materials representing the features of the metallic coating and the pearl-color coating, it is desired to obtain this reflection characteristic with high precision. However, the value of the reflection characteristic largely changes even upon a slight change in the angle of the illuminating direction. For a high-precision measurement, it is necessary to precisely set the orientation of the multi-angle calorimeter with respect to the surface of the measurement object, i.e., to precisely coincide the center axis of the main body and the normal to the surface of the measurement object.

For example, in the case that a coating surface on a body of an automotive vehicle is measured by a portable colorimeter, a contact surface of the calorimeter is formed by rubber or like material so as not to damage the coating surface. Accordingly, it has not been easy to precisely coincide the center axis of the main body and the normal to the object surface. Particularly, it has been even more difficult when the surface of the measurement object is curved as the body of the automotive vehicle is.

In order to overcome the above problem, calorimeters having a function of adjusting an angle of the main body with respect to the object surface have been put into practice. However, there are still problems of an increased number of parts and a complicated construction because a sensor for detecting an angle is necessary, and also a problem of a long measurement time since time is required for angle adjustment in each measurement.

SUMMARY OF THE INVENTION

It is an object of the present invention to provide a measurement apparatus which is free from the problems residing in the prior art.

It is another object of the present invention to provide a color measurement apparatus which enables a high precision color measurement by correcting a measurement result according to an angle of inclination of a main boy of the apparatus with respect to a surface of an object.

It is another object of the present invention to provide a color measurement apparatus which can precisely obtain a refection characteristic of a highlight direction even if an apparatus main body is slightly inclined with respect to an object surface.

The invention is directed to a measurement apparatus for measuring color of an object is provided with a main body having an opening opposed to an object to be measured.

According to an aspect of the invention, a measurement apparatus is provided with a plurality of illuminators for illuminating a surface of the object in directions different from one another, a light detector for detecting reflected light in a specified direction from the object illuminated by the plurality of illuminators and outputting light detection signals corresponding to light intensities. In the apparatus, further, there are provided a first calculator for calculating reflection characteristic measurement values of the measurement object in correspondence with the plurality of illuminators based on the light detection signals, a storage device for storing an approximate function having an angle of an illuminating direction with respect to a reference direction as a variable if the reference direction is a direction symmetrical with the specific direction with respect to a center axis of the main body in parallel to a normal to the opening, and having a plurality of undetermined coefficients including an angle of inclination of the center axis of the main body with respect to a normal to the surface of the object, and a second calculator for determining a plurality of undetermined coefficients based on the respective reflection characteristic measurement values and the angles of the illuminating directions, and correcting the respective reflection characteristic measurement values using the approximate function whose undetermined coefficients are determined.

According to another aspect of the invention, a measurement apparatus is provided with a plurality of illuminators for illuminating a surface of the object in directions different from one another. The plurality of illuminators includes a first illuminator provided at one side of a reference direction where a center axis of the main body is located and a second illuminator provided on the other side of the reference direction if the reference direction is a direction symmetrical with the specific direction with respect to the center axis of the main body in parallel to a normal to the opening. The first and second illuminators are provided in positions symmetrical with each other with respect to the reference direction. The apparatus is further provided with a light detector for detecting reflected light in a specified direction from the object illuminated by the plurality of illuminators and outputting light detection signals corresponding to light intensities, and a calculator for calculating a reflection characteristic of the object corresponding to the first illuminator based on a sum of the light detection signals corresponding to the first and second illuminator.

According to still another aspect of the invention, a measurement apparatus is provided with an illuminator for illuminating a surface of the object in a specific direction, a plurality of light detectors for detecting reflected light in directions different from one another from the object illuminated by the illuminator and outputting light detection signals corresponding to light intensities. Further, there are provided a first calculator for calculating reflection characteristic measurement values of the object in correspondence with the plurality of light detectors based on the light detection signals, a storage device for storing an approximate function having an angle of a light detecting direction with respect to a reference direction as a variable if the reference direction is a direction symmetrical with the specific direction with respect to a center axis of the main body in parallel to a normal to the measurement opening, and having a plurality of undetermined coefficients including an angle of inclination of the center axis of the main body with respect to a normal to the surface of the object, and a second calculator for determining a plurality of undetermined coefficients based on the respective reflection characteristic measurement values and the angles of the light detecting directions, and correcting the respective reflection characteristic measurement values using the approximate function whose undetermined coefficients are determined.

According to further aspect of the invention, a measurement apparatus is provided with an illuminator for illuminating a surface of the object in a specific direction, and a plurality of light detectors for detecting reflected light in directions different from one another from the object illuminated by the illuminator and outputting light detection signals corresponding to light intensities. The plurality of light detectors include a first light detector provided at one side of a reference direction where a center axis of the main body is located and a second light detector provided on the other side of the reference direction if the reference direction is a direction symmetrical with the specific direction with respect to the center axis of the main body in parallel to a normal to the opening. The first and second light detectors are provided in positions symmetrical with each other with respect to the reference direction. The apparatus is further provided with a calculator for calculating a reflection characteristic of the object corresponding to the first light detector based on a sum of the light detection signals corresponding to the first and second light detectors.

These and other objects, features and advantages of the present invention will become more apparent upon a reading of the following detailed description and accompanying drawings.

DETAILED DESCRIPTION OF THE PREFERRED EMBODIMENTS OF THE INVENTION

Figure 1:
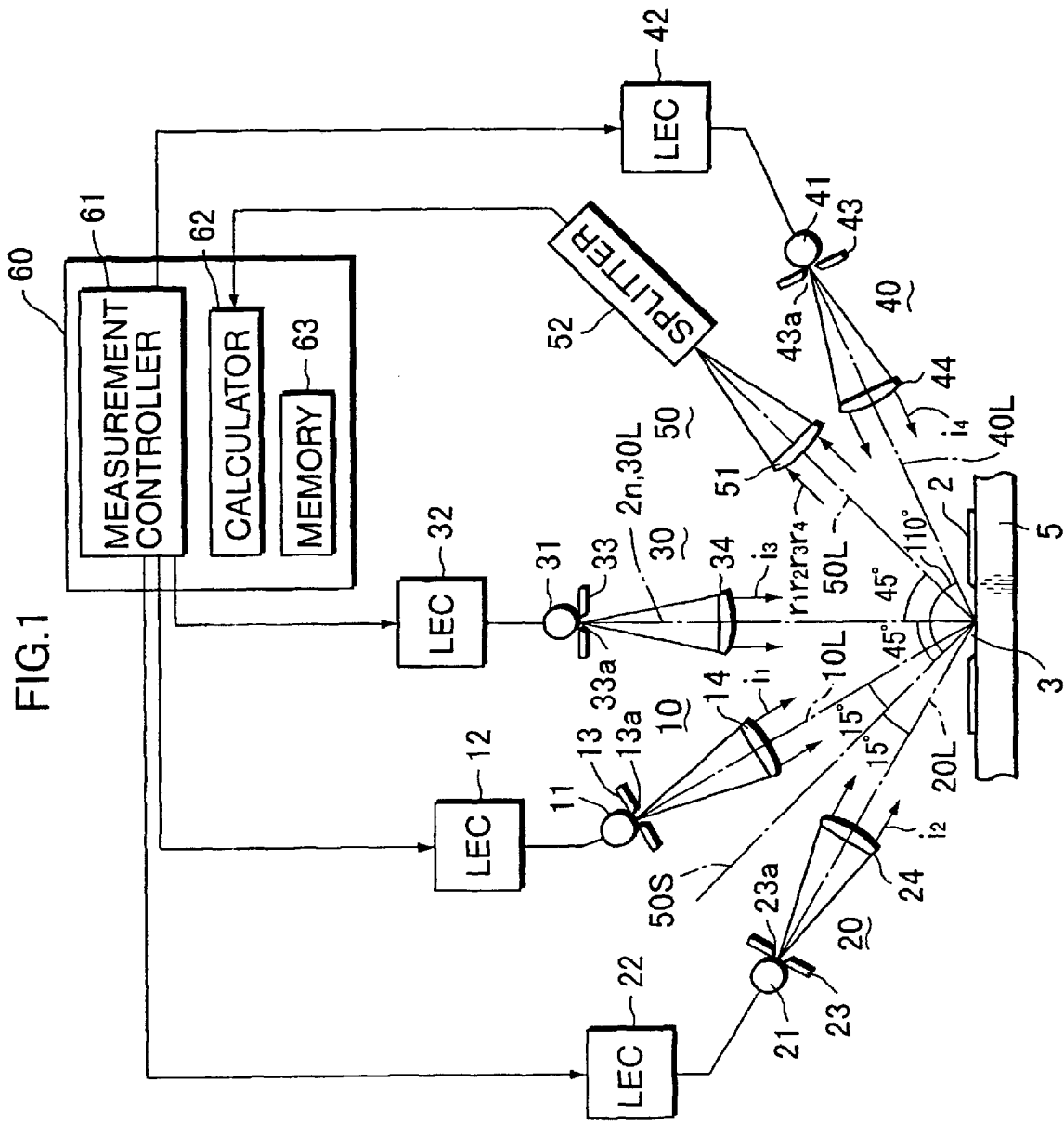
FIG. 1 is a diagram showing an inner construction of a multi-angle colorimeter according to a first embodiment of the invention.
Figure 2A:
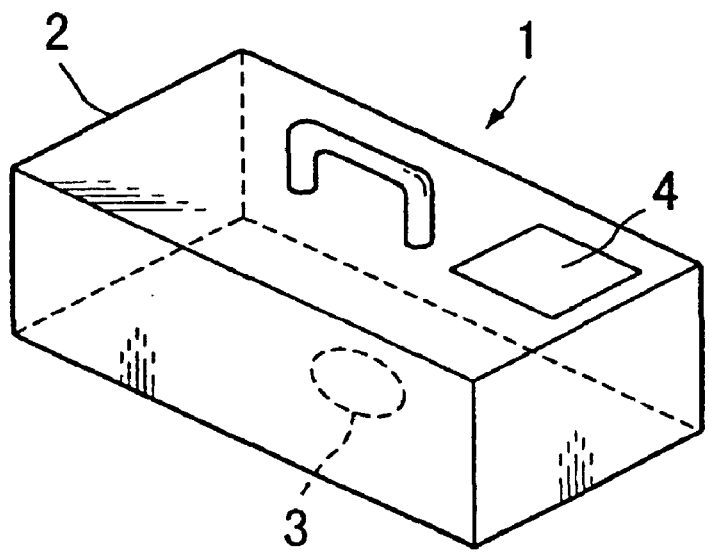
FIG. 2A is a perspective view showing an outer configuration of the multi-angle colorimeter shown in FIG. 1.
Figure 2B:
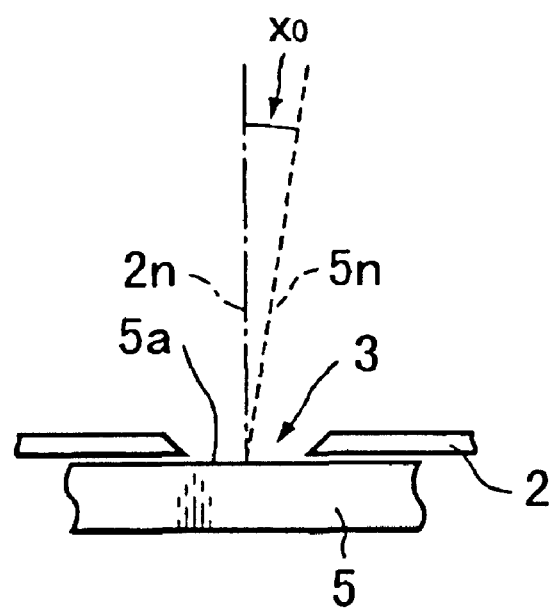
FIG. 2B is a diagram showing an angle of inclination between a center axis of a main body of the multi-angle calorimeter shown in FIG. 1 and a surface of a measurement object.

FIG. 1 is a diagram showing an inner construction of a multi-angle colorimeter according to a first embodiment of the invention, FIG. 2A is a perspective view showing an outer configuration of the multi-angle colorimeter, and FIG. 2B is a diagram showing an angle of inclination between a center axis of a colorimeter main body of the multi-angle colorimeter and a surface of a measurement object.

The multi-angle calorimeter according to the first embodiment is of the type in which four illuminators are provided for illuminating a surface of a measurement object in directions different from each other, and light reflected by the object surface are detected in one direction. This multi-angle calorimeter operates as follows. An approximate function having four undetermined coefficients and having an angle of the illuminating direction as a variable is stored. First, reflection characteristic measurement values by the respective illuminators are obtained. The four undetermined coefficients are determined such that values obtained by substituting the angles of the respective illuminating directions into the approximate function are maximally approximate to or equal to the respective reflection characteristic measurement values. An error created by an angle of inclination between the center axis of the main body and the surface of the measurement object is corrected by correcting the reflection characteristic measurement values using the approximate function having the determined coefficients.

As shown in FIG. 2A, the multi-angle colorimeter 1 includes a box-shaped colorimeter main body 2 in which the respective parts (to be described later) of FIG. 1 are accommodated. The main body 2 is provided with a measurement opening 3 formed in its bottom wall, and a display 4 provided in a specified position of its upper surface for showing a measurement result, and constructs a portable calorimeter.

As shown in FIG. 2B, a measurement is conducted while directing the measurement opening 3 of the multi-angle colorimeter 1 toward a measurement object 5. In the first embodiment, when it is assumed that $x_0$ denotes an angle of inclination of a normal $5n$ to a surface $5a$ of the measurement object 5 with respect to a center axis $2n$ (normal to the measurement opening 3) of the main body 2, an error created by the angle of inclination $x_0$ is corrected.

In FIG. 1, the multi-angle colorimeter 1 is provided with first to fourth illuminators 10, 20, 30, 40, a light detector 50 and a controller 60.

The multi-angle colorimeter 10 includes a light source 11 made of, e.g., a xenon flash lamp, a light emitting circuit 12 for driving the light source 11, a beam restricting plate 13 for restricting a beam from the light source 11, and a collimator lens 14. The beam restricting plate 13 is arranged such that its opening 13a coincides with a focusing position of the collimator lens 14. The beam from the light source 11 having passed through the beam restricting plate 13a of the beam restricting plate 13 is collimated by the collimator lens 14 to become a parallel beam $i_1$ to illuminate the measurement object 5.

Similar to the first illuminator 10, the second to fourth illuminators 20, 30, 40 include light sources 21, 31, 41, light emitting circuits 22, 32, 42, beam restricting plates 23, 33, 43, and collimator lenses 24, 34, 44, respectively. Beams from the light sources 21, 31, 41 having passed through the openings 23a, 33a, 43a of the beam restricting plates 23, 33, 43 are collimated by the collimator lenses 24, 34, 44 to become parallel beams $i_2$, $i_3$, $i_4$, to illuminate the measurement object 5, respectively.

The light detector 50 includes a detecting optical system 51 for converting a parallel beam from the measurement object 5 and a splitter provided in a focusing position of the detecting optical system 51 for splitting the incident beam for each wavelength and outputting spectral data according to a light intensity.

The controller 60 is comprised of, e.g., a CPU and is provided with a measurement controller 61, a calculator 62 and a memory 53 as function blocks. The controller 60 controls the entire operation of the multi-angle calorimeter 1 in accordance with a procedure to be described later. The measurement controller 61 is electrically connected with the light emitting circuits 12, 22, 32, 42 and has a function of controlling the light emission of the light sources 11, 21, 31, 41.

The calculator 62 has following functions: (1) Function as a first calculator for calculating the reflection characteristic measurement values of the measurement object 5 corresponding to the illuminators 10 to 40 using the spectral data from the splitter 52 which is electrically connected with the calculator 62, and (2) Function as a second calculator for determining the undetermined coefficients of a Gaussian function using the reflection characteristic measurement values and calculating corrected reflection characteristic values by correcting an error created by the angle of inclination $x_0$ of the measurement object $5n$ to the measurement object $5a$ of the measurement object 5 with respect to the center axis $2n$ of the main body 2 using this Gaussian function. The second function and the Gaussian function are described later.

The memory 63 is comprised of, e.g., a RAM, EEPROM or ROM. The measurement results and the like are temporarily saved, and an operation program of the controller 60 including the measurement controller 61 and the calculator 62 and the Gaussian function expressed by equation (3) to be described later are stored in the memory 63.

Next, the arrangement of the first to fourth illuminators 10 to 40 and the light detector 50 is described.

The light detector 50 is arranged such that its optical axis 50L coincides with a direction at 45° to the center axis 2n of the main body 2 (specific direction). If the positions of the first to fourth illuminators 10 to 40 are expressed by angles from a reference direction 50S which is a direction symmetrical with the light detector 50L of the light detector 50 with respect to the center axis 2n of the main body 2 assuming that a side where the center axis 2n is located is a positive side, the first to fourth illuminators 10 to 40 are arranged such that their optical axes 10L, 20L, 30L, 40L coincide with directions of +15°, −15°, +45°, +110°, respectively. Accordingly, the center axis 2n and the optical axis 30L coincide with each other.

Next, an angle distribution of bright materials and approximation of a reflection characteristic by a function which are performed in the first embodiment are described.

Figure 13:
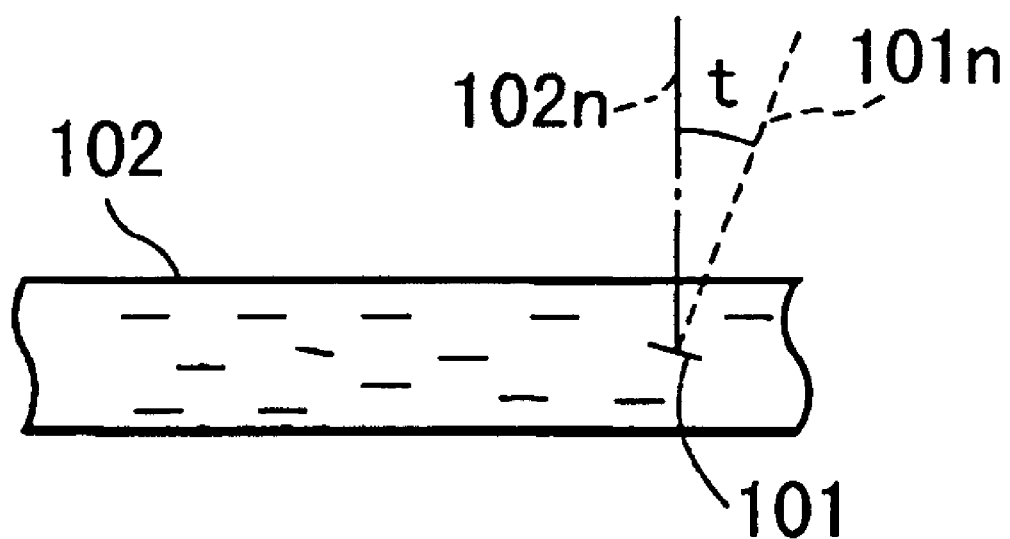
FIG. 13 is a diagram showing a film containing bright materials comprised of thin pieces of aluminum or mica in a metallic or pearl-color coating.
Figure 14:
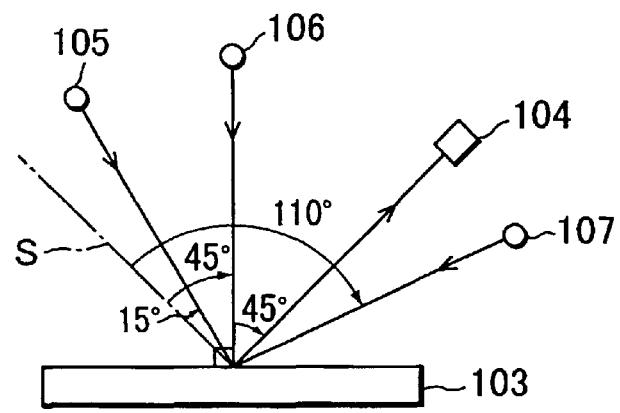
FIG. 14 is a construction diagram of a conventional multi-angle colorimeter.
Figure 15:
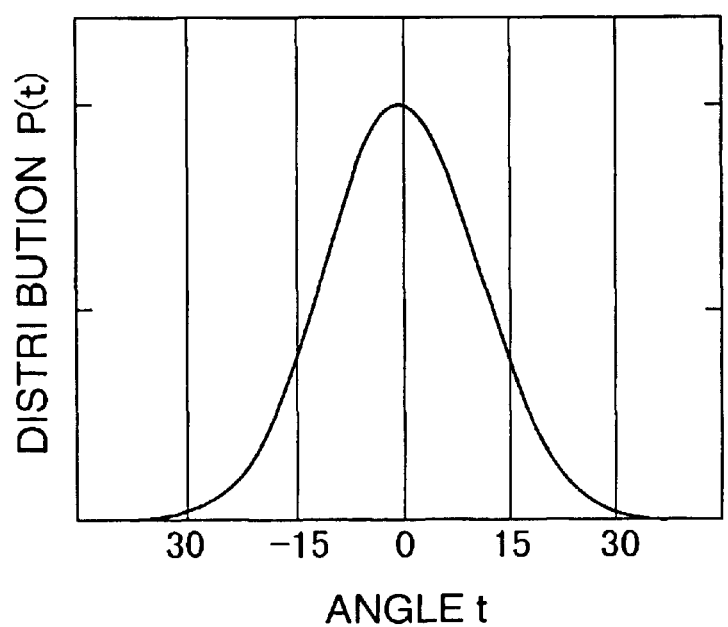
FIG. 15 is a graph showing an angle distribution of bright materials in the film.

As described with reference to FIG. 15, an angle distribution of the bright materials in a film of a metallic coating or pearl-color coating approximates to a normal distribution. Accordingly, this angle distribution P(t) of the bright materials can be approximated to a symmetric exponential function, e.g., a Gaussian function expressed by following equation (1):

$$P(t)=P_o \cdot \exp[-(t/D)^2] \quad (1)$$

where $P_o$, D, t denote a coefficient which gives a maximum value of the Gaussian function, a coefficient which gives a width of the Gaussian function, and an angle between the normal 102n to the outer surface of the film 102 and the normal 101n to the outer surface of the bright material 101 as shown in FIG. 13, respectively.

Figure 16:
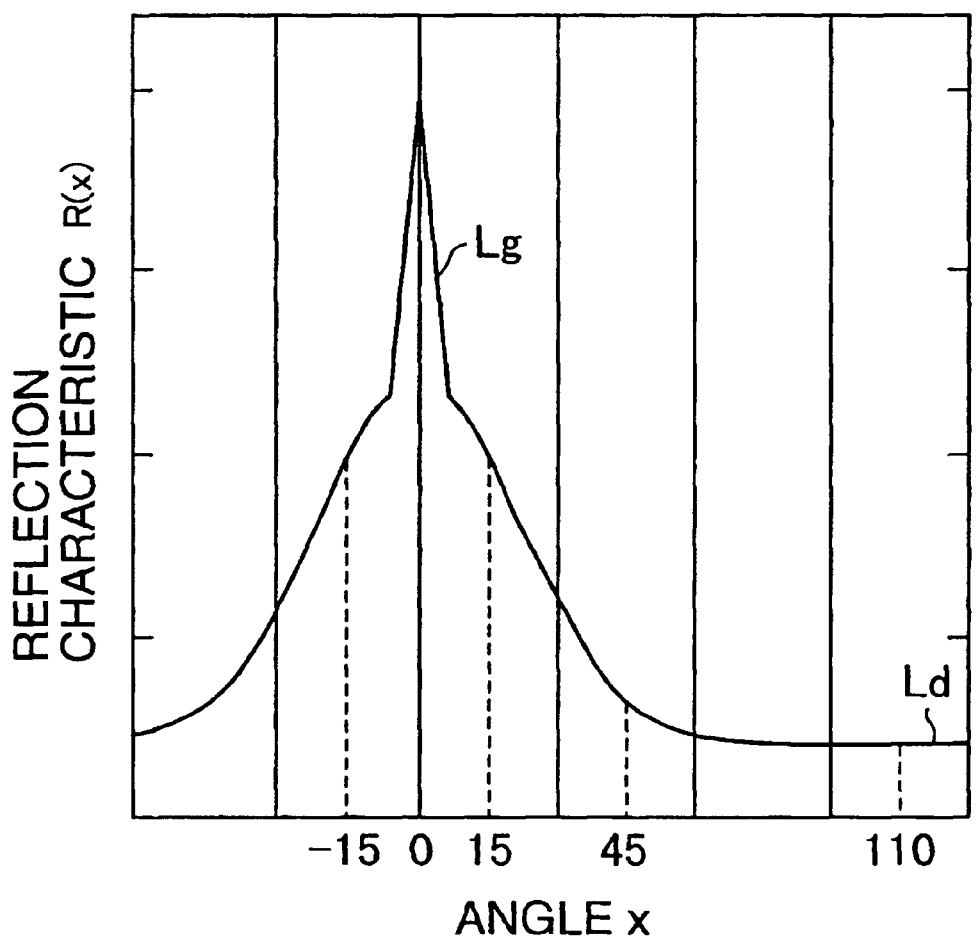
FIG. 16 is a graph showing measurement results when a reflection characteristic is measured by illuminating a measurement object in various directions.

By approximating the angle distribution P(t) of the bright materials by the Gaussian function as shown in equation (1), a reflection characteristic R(x) shown in FIG. 16 can be approximated to a Gaussian function $R_g(x)$ having a peak in a regular reflection direction as shown in following equation (2) except an angle range at and near 0 (regularly reflected light $L_g$).

$$R_g(x)=R_0 \cdot \exp[-(x/d)^2]+b \quad (2)$$

where $R_0$, d, b, x denote a coefficient which gives a maximum value of the Gaussian function, a coefficient which gives a width of the Gaussian function, a coefficient which gives an offset of the Gaussian function corresponding to diffused reflection, and an angle when the regular reflection direction is 0 and a side where the normal to the object surface is located is a positive side.

If x is an angle based on the reference direction SOS (where x=0) which is a direction symmetrical with the optical axis 50L of the light detector 50 with respect to the center axis 2n of the main body 2 which should coincide with the normal 5n (see FIG. 2B) to the object surface 5a, and a side where the center axis 2n is located is assumed to be a positive side, equation (2) can be rewritten into the following equation (3):

$$R_g(x)=R_0 \cdot \exp[-[(x-x_0)/d]^2]+b \quad (3)$$

where $x_0$ is a coefficient which corresponds to a center of the angle distribution of the actual reflected light from the bright materials and gives a center angle of the Gaussian function, and indicates an angle difference between the normal 5n (see FIG. 2B) to the object surface 5a and the center axis 2n of the main body 2. If the normal 5n and the center axis 2n coincide, $x_0$=0. However, in reality, they do not coincide and, accordingly, $x_0 \ne 0$.

Description has been made up to now on the assumption that the center of the angle distribution of the reflected light from the bright materials and the normal 5n to the object surface 5a coincide. Unless they coincide, $x_0$ represents not the normal 5n to the object surface 5a, but an angle difference between the center of the angle distribution of the reflected light from the bright materials and the center axis 2n and the main body 2. Since visual evaluation on the metallic coating and the pearl-color coating is made by the reflected light, a correspondence between the visual evaluation and the measurement values can be improved by making a correction based on the reflected light.

As can be seen from equation (3), the Gaussian function $R_g(x)$ can be determined by determining the four undetermined coefficients $R_0$, $x_0$, d, b. By calculating the reflection characteristic measurement values R(x) when the measurement object is illuminated in four or more directions, the four undetermined coefficients which give calculation values $R_g(x)$ most approximate to the reflection characteristic measurement values R(x) can be obtained.

Figure 3:
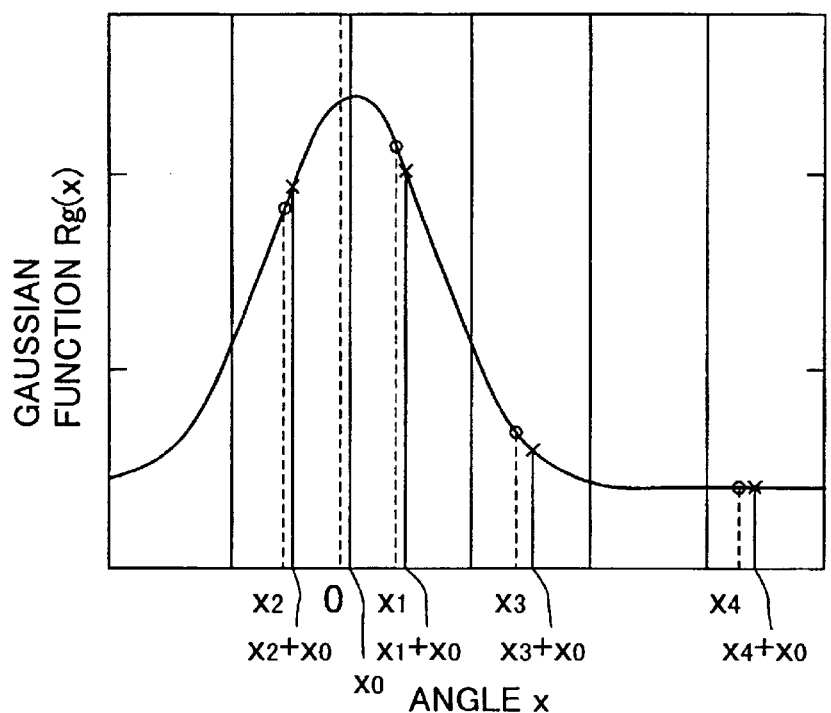
FIG. 3 is a graph showing a correction of measurement results using a Gaussian function.
Figure 4:
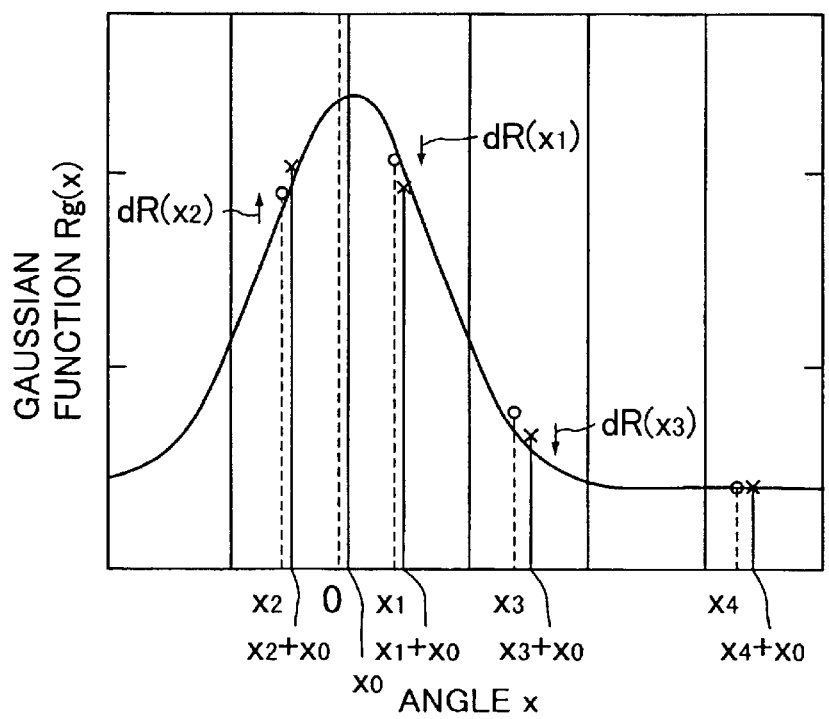
FIG. 4 is a graph showing a correction of measurement results using the Gaussian function.

Next, the operation of the multi-angle colorimeter is described with reference to FIGS. 1, 3 to 5. FIGS. 3 and 4 are graphs showing correction of the measurement values using a Gaussian function, and FIG. 5 is a flowchart showing an operation procedure.

Figure 5:
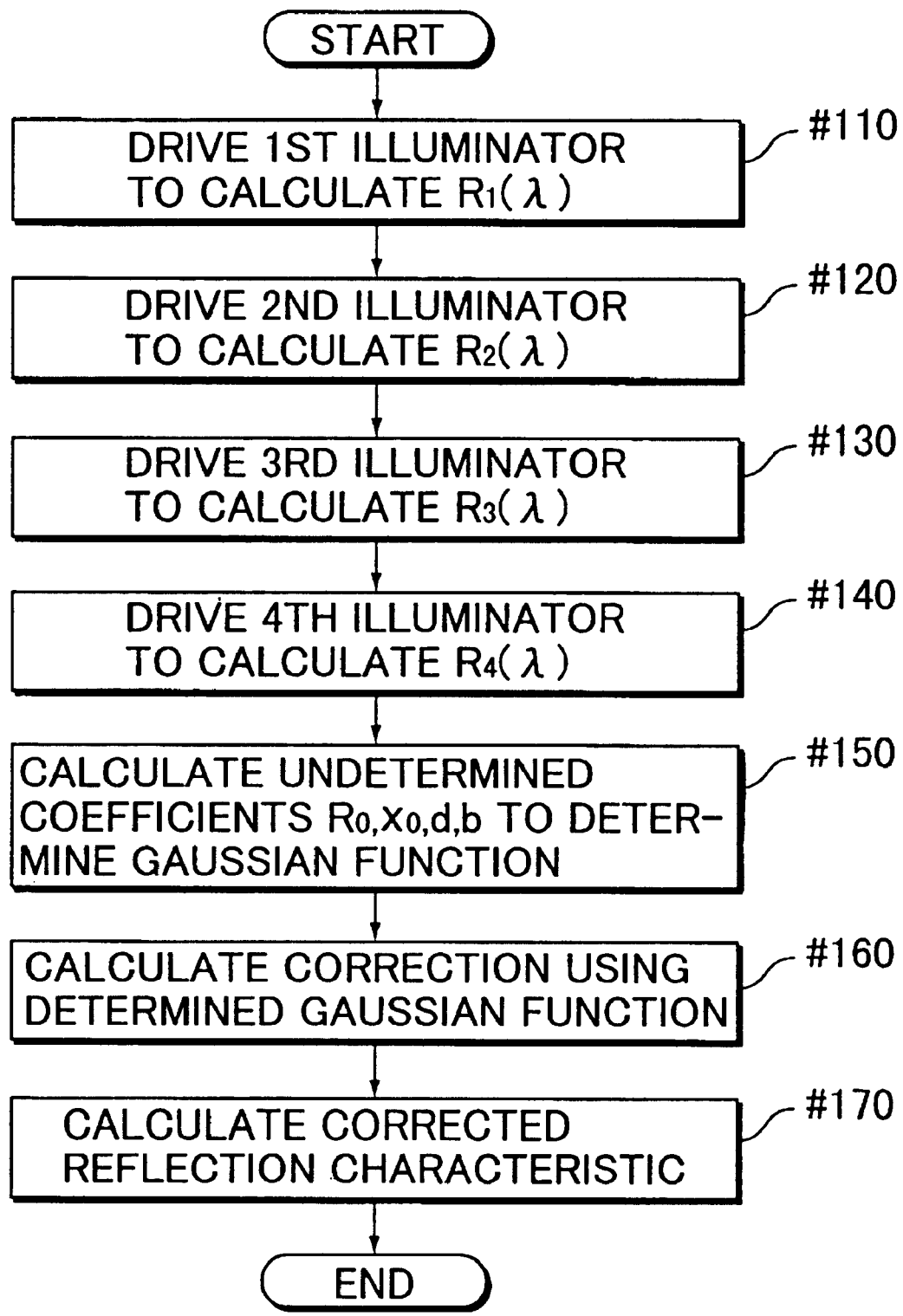
FIG. 5 is a flowchart showing an operation procedure of the multi-angle calorimeter shown in FIG. 1.

In Steps #110 to #140 of FIG. 5, the first to fourth illuminators 10, 20, 30, 40 are successively driven by the measurement controller 61. The measurement object 5 is successively illuminated in different directions by the parallel beams $i_1$, $i_2$, $i_3$, $i_4$, and spectral characteristics $r_1(\lambda)$, $r_2(\lambda)$, $r_3(\lambda)$, $r_4(\lambda)$ of reflected light $r_1$, $r_2$, $r_3$, $r_4$ incident on the light detector 51 are successively sent to the calculator 62 from the splitter 52. Spectral reflection characteristic measurement values $R_1(\lambda)$, $R_2(\lambda)$, $R_3(\lambda)$, $R_4(\lambda)$ are calculated for the respective illuminating directions based on the spectral characteristics $r_1(\lambda)$, $r_2(\lambda)$, $r_3(\lambda)$, $r_4(\lambda)$ by the function of the calculator 62 as the first calculator.

Here, the calculator 62 assumes the spectral reflection characteristic measurement values $R(\lambda)$ as a function $R(\lambda,x)$ having the angle x of the illuminating direction as a variable. In the following, $R(\lambda,x)$ is written as R(x) for the sake of convenience. In other words, $R_1(\lambda)$, $R_2(\lambda)$, $R_3(\lambda)$, $R_4(\lambda)$ are written as $R(x_1)$, $R(x_2)$, $R(x_3)$, $R(x_4)$ and indicated by O in FIG. 3.

Referring back to FIG. 5, the four undetermined coefficients $R_0$, $x_0$, d, b for determining the Gaussian function $R_g(x)$ are calculated by the so-called least squares method such that a sum S of squares of difference between the measurement values $R(x_i)$, $R(x_2)$, $R(x_3)$, $R(x_4)$ and $R_g(x_1)$, $R_g(x_2)$, $R_g(x_3)$, $R_g(x_4)$ obtained by substituting $x_1$, $x_2$, $x_3$, $x_4$ into the Gaussian function $R_g(x)$ shown in equation (3), i.e., $$R_g(x_1)=R_0 \cdot \exp[-[(x_1-x_0)/d]^2]+b$$

$$R_g(x_2)=R_0 \cdot \exp[-[(x_2-x_0)/d]^2]+b$$

$$R_g(x_3)=R_0 \cdot \exp[-[(x_3-x_0)/d]^2]+b$$

$$R_g(x_4)=R_0 \cdot \exp[-[(x_4-x_0)/d]^2]+b, \text{ i.e.,}$$

$$S=[R_g(x_1)-R(x_1)]^2+[R_g(x_2)-R(x_2)]^2+[R_g(x_3)-R(x_3)]^2+[R_g(x_3)-R(x_3)]^2$$
is minimized.

It should be noted that $x_1$=+15°, $x_2$=−15, $x_3$=+45°, $x_4$=110°. There is given an additional condition that the center angle $x_0$ of the Gaussian function $R_g(x)$ is located between $x_1$=+15° and $x_2$=−15°.

Subsequently, the measurement values are corrected using the determined Gaussian function by the calculator 62. Corrected reflection characteristic values $R_g(x_1+x_0)$, $R_g(x_2+x_0)$, $R_g(x_3+x_0)$, $R_g(x_4+x_0)$ corresponding to angles $x_1+x_0$, $x_2+x_0$, $x_3+x_0$, $x_4+x_0$ based on the center of the Gaussian function are obtained from the determined Gaussian function and the angle difference $x_0$. In other words, the Gaussian function is determined using the measurement values indicated by O in FIG. 3, and the corrected reflection characteristic values indicated by x in FIG. 3 can be calculated based on the Gaussian function. Normally, since the angle difference $x_0$ is sufficiently small, the correction can be precisely made even if there is a slight error in the Gaussian function representing the angle distribution of the reflection characteristic.

However, as shown in FIG. 4, the reflection characteristic measurement values $R(x_1)$, $R(x_2)$, $R(x_3)$, $R(x_4)$ indicated by O at $x=x_1$, $x_2$, $x_3$, $x_4$ and the determined Gaussian function indicated by solid line may not coincide.

Accordingly, in Step #160 of FIG. 5, reflection characteristic approximate values $R_g(x_1)$, $R_g(x_2)$, $R_g(x_3)$, $R_g(x_4)$ at $x=x_1$, $x_2$, $x_3$, $x_4$ are calculated based on the determined Gaussian function, and reflection characteristic approximate values $R_g(x_1+x_0)$, $R_g(x_2+x_0)$, $R_g(x_3+x_0)$, $R_g(x_4+x_0)$ at $x=x_1+x_0$, $x_2+x_0$, $x_3+x_0$, $x_4+x_0$ are further calculated. Differences between these reflection characteristic approximate values, i.e., $$dR_g(x_1)=R_g(x_1+x_0)-R_g(x_1)$$

$$dR_g(x_2)=R_g(x_2+x_0)-R_g(x_2)$$

$$dR_g(x_3)=R_g(x_3+x_0)-R_g(x_3)$$

$$dR_g(x_4)=R_g(x_4+x_0)-R_g(x_4)$$

are calculated as correction values.

Subsequently, in Step #170, these correction values are added to the reflection characteristic measurement values, respectively: i.e., $$R'(x_1)=R_g(x_1)+dR_g(x_1)$$

$$R'(x_2)=R_g(x_2)+dR_g(x_2)$$

$$R'(x_3)=R_g(x_3)+dR_g(x_3)$$

$$R'(x_4)=R_g(x_4)+dR_g(x_4)$$

to calculate corrected reflection characteristic values $R'(x_1)$, $R'(x_2)$, $R'(x_3)$, $R'(x_4)$. In this way, the reflection characteristic measurement values can be precisely corrected.

Even if there are errors between the approximate values on the Gaussian function and the measurement values in the approximation of the Gaussian function as shown in FIG. 4, these errors are thought to be canceled by taking differences between the values at $x=x_1$, $x_2$, $x_3$, $x_4$ and those at $x=x_1+x_0$, $x_2+x_0$, $x_3+x_0$, $x_4+x_0$. Thus, the correction amounts can be highly precisely calculated.

As described above, since the reflection characteristic measurement value $R(x)$ is the spectral reflection characteristic $R(\lambda,x)$ dependent on wavelength $\lambda$, the respective operations shown in FIG. 5 are performed for each wavelength.

According to the first embodiment, when the direction symmetrical with the optical axis 50L of the light detector 50 with respect to the center axis 2n of the main body 2 parallel to the normal to the measurement opening 3 is assumed to be a reference direction, the Gaussian function defined by equation (3) as an approximate function having four undetermined coefficients and having the angles of the optical axes 10L to 40L of the first to fourth illuminators 10 to 40 based on the reference direction as variables is stored in the memory 63, the four undetermined coefficients of the Gaussian function are determined based on the reflection characteristic measurement values of the measurement object 5 corresponding to the first to fourth illuminators and the angles of the illuminating directions, and the reflection characteristic measurement values corresponding to the respective illuminators are corrected using the determined Gaussian function. Accordingly, the corrected reflection characteristic values in which the error resulting from the inclination of the main body 2 with respect to the measurement object 5 is precisely canceled can be calculated.

Figure 6:
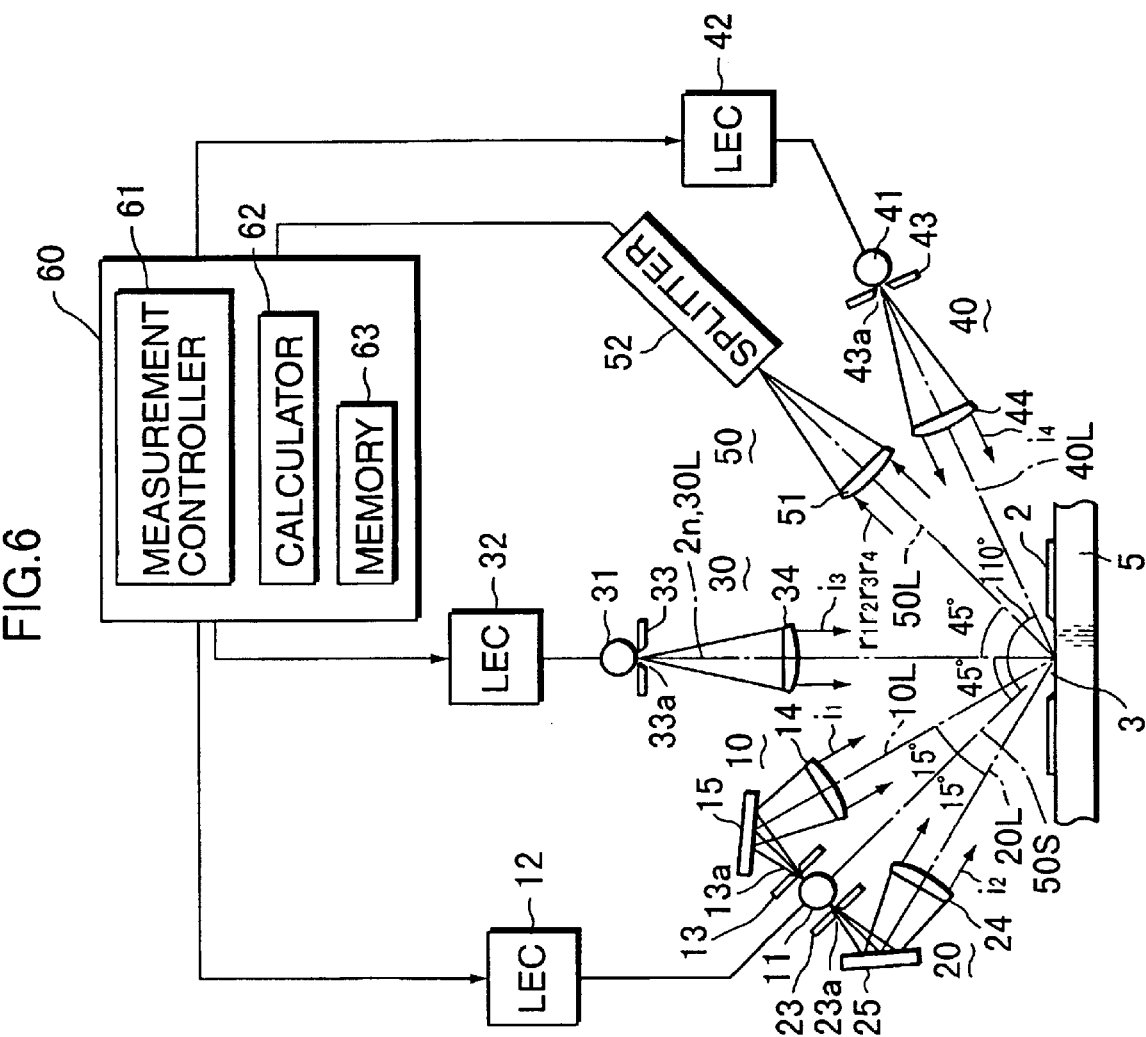
FIG. 6 is a diagram showing an inner construction of a multi-angle colorimeter according to a second embodiment of the invention.

FIG. 6 is a diagram showing the inner construction of a multi-angle colorimeter according to a second embodiment of the invention. The second embodiment is similar to the first embodiment shown in FIG. 2 in its outer configuration. The same parts as those of FIG. 1 are identified by the same reference numerals, and the second embodiment is described only in points different from the first embodiment.

In the second embodiment, first and second illuminator 10, 20 are provided with reflectors 15, 25, respectively, and share a common light source 11. When the light source 11 is driven by a light emitting circuit 12, a beam from the light source 11 having passed through an opening 13a of a beam restricting plate 13 is reflected by the reflector 15 and collimated by a collimator lens 14 to become a parallel beam $i_1$ to illuminate a measurement object 5 along an optical axis 10L. A beam from the light source 11 having passed through an opening 23a of a beam restricting plate 23 is reflected by the reflector 25 and collimated by a collimator lens 24 to become a parallel beam $i_2$ to illuminate the measurement object 5 along an optical axis 20L. Accordingly, the measurement object 5 is simultaneously illuminated by the parallel beams $i_1$, $i_2$ from the first and second illuminators 10, 20, and a light detector 50 detects reflected light $r_1$, $r_2$ from the measurement object 5 simultaneously.

A calculator 62 of the second embodiment has a function of calculating a reflection characteristic of the measurement object 5 using spectral data from the splitter 52.

Next, the operation of the second embodiment is described. In the case that a center axis 2n of a colorimeter main body 2 is inclined only by an angle $x_0$ without coinciding with a normal 5n (see FIG. 2B) to an object surface 5a in the second embodiment, the reflected light of the parallel beam of one of the first and second illuminators 10, 20 increases, whereas the reflected light of the parallel beam of the other illuminator decreases. Accordingly, a total intensity of the reflected light $r_1$, $r_2$ incident on the light detector 50 when the light source 11 is driven barely changes.

As described with reference to FIG. 16, the reflection characteristic in the highlight direction is more largely influenced by the angle of inclination of the main body 2 with respect to the object surface 5a. However, according to the second embodiment, an influence of the angle of inclination on the reflection characteristic measurement value in the highlight direction is reduced without calculation using an approximate function as in the first embodiment, and measurements can be precisely performed.

Further, since the first and second illuminators 10, 20 have the common light source 11, a power consumption and a measurement time can be reduced, and the construction can be simplified due to a reduced number of parts.

Figure 7:
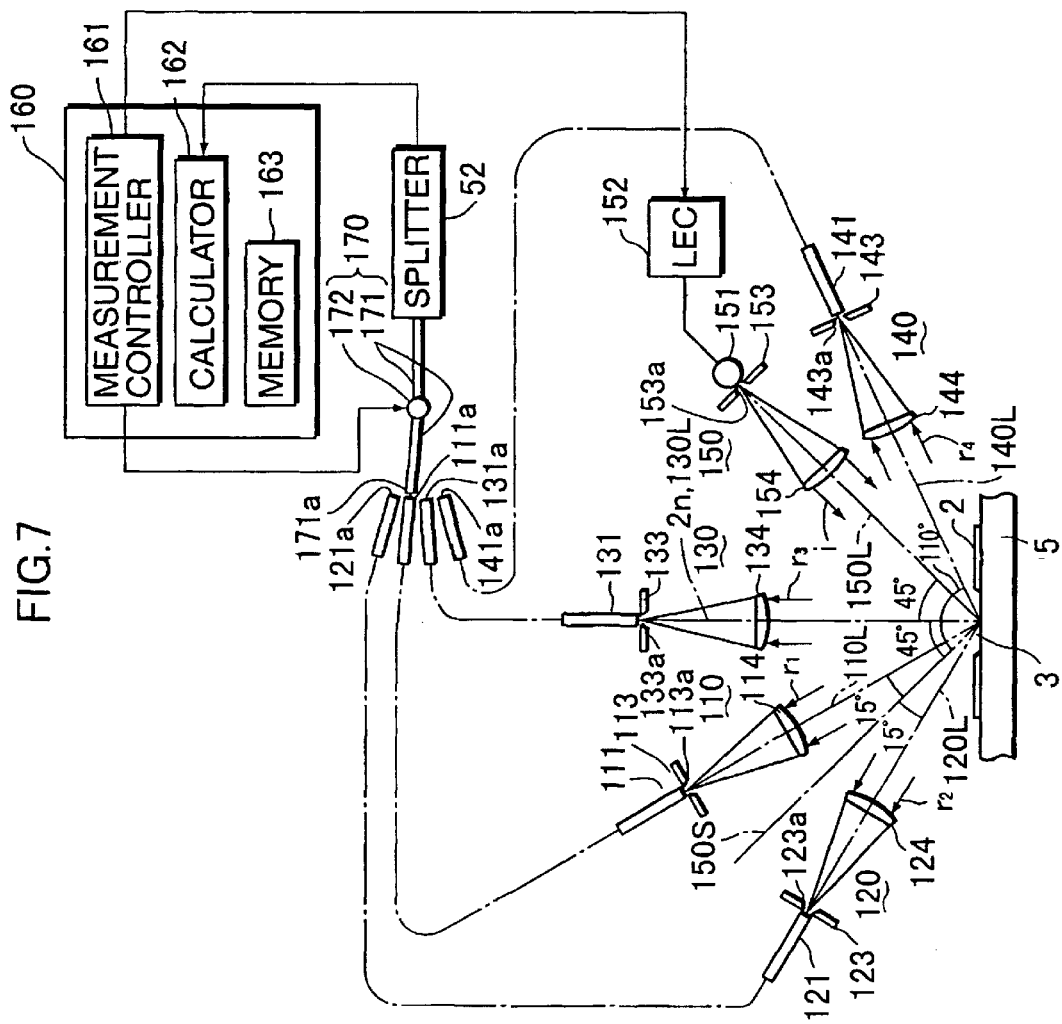
FIG. 7 is a diagram showing an inner construction of a multi-angle colorimeter according to a third embodiment of the invention.

FIG. 7 is a diagram showing the inner construction of a multi-angle colorimeter according to a third embodiment of the invention. The second embodiment is similar to the first embodiment shown in FIG. 2 in its outer configuration. The same parts as those of FIG. 1 are identified by the same reference numerals, and the third embodiment is described only in points different from the first embodiment.

The multi-angle calorimeter according to the third embodiment is of the type in which a surface of a measurement object is illuminated by one illuminator and four light detector are provided for detecting reflected light from the object surface in directions different from each other. As opposed to the first embodiment in which the approximate function having four undetermined coefficients and having the angle of the illuminating direction as a variable, an approximate function having four undetermined coefficients and having an angle of a light detecting direction as a variable is stored in the third embodiment. However, the third embodiment operates similar to the first embodiment. Specifically, in the third embodiment, the reflection characteristic measurement values by the respective light detectors are calculated, the four undetermined coefficients are determined such that values obtained by substituting the angles of the respective light detecting directions into the approximate function maximally approximate to the respective reflection characteristic measurement values, and the reflection characteristic measurement values are corrected using the approximate function whose undetermined coefficients are determined. In this way, errors created by the angle of inclination of the center axis of the main body with respect to the surface of the measurement object are corrected.

In FIG. 7, a multi-angle colorimeter 1 is provided with first to fourth light guiding devices 110. 120, 130 and 140, an illuminator 150, a controller 160, a beam switcher 170 and a splitter 52.

The illuminator 150 includes a light source 151 made of, e.g., a xenon flash lamp, a light emitting circuit 152 for driving the light source 151, a beam restricting plate 153 for restricting a beam from the light source 151, and a collimator lens 154. The beam restricting plate 153 is arranged such that its opening 153a coincides with a focusing position of the collimator lens 154. The beam from the light source 151 having passed through the opening 153a of the beam restricting plate 153 is collimated by the collimator lens 154 to become a parallel beam i to illuminate a measurement object 5.

The first light guiding device 110 includes an optical fiber 111, a beam restricting plate 113 and a detecting optical system 114 for converting a parallel beam $r_1$ from the measurement object 5. The beam restricting plate 113 is arranged such that its opening 113a coincides with a focusing position of the detecting optical system 114. The beam $r_1$ from the measurement object 5 having passed through the opening 113a of the beam restricting plate 113 is incident on an incident end of the optical fiber 111 and guided to an emerging end 111a.

Similar to the first light guiding device 110, the second to fourth light guiding devices 120, 130, 140 include optical fibers 121, 131, 141, beam restricting plates 123, 133, 143, and detecting optical systems 124, 134, 144, respectively. Beams $r_2$, $r_3$, $r_4$ from the measurement object 5 having passed through the openings 123a, 133a, 143a of the beam restricting plates 123, 133, 143 are incident on incident ends of the optical fiber 112, 131, 141 and guided to emerging ends 121a, 131a, 141a.

A beam switcher 170 includes a movable fiber 171 whose incident end 171a is movable to positions facing the emerging ends 111a, 121a, 131a, 141a of the optical fibers 111, 121, 131, 141, and a driving device 172 for moving the movable fiber 171. The beams from the emerging ends 111a, 121a, 131a, 141a of the optical fibers 111, 121, 131, 141 are successively guided to a splitter 52 by the movement of the movable fiber 171.

The first light guiding device 110, the beam switcher 170 and the splitter 52 construct a first light detector; the second light guiding device 120, the beam switcher 170 and the splitter 52 construct a second light detector; the third light guiding device 130, the beam switcher 170 and the splitter 52 construct a third light detector; and the fourth light guiding device 140, the beam switcher 170 and the splitter 52 construct a fourth light detector.

The controller 160 is comprised of, e.g., a CPU and is provided with a measurement controller 161, a calculator 162 and a memory 163 as function blocks. The controller 160 controls the entire operation of the multi-angle calorimeter 1. The measurement controller 161 is electrically connected with a light emitting circuit 152 and has a function of controlling the light emission of the light source 151 and a function of controlling the movement of the movable fiber 171 by being electrically connected with the driving device 172.

Similar to the calculator 62 of the first embodiment, the calculator 162 has following functions: (1) Function as a first calculator for calculating reflection characteristic measurement values of the measurement object 5 corresponding to the respective light guiding devices 110 to 140 using the spectral data from the splitter 52 which is electrically connected with the calculator 162, and (2) Function as a second calculator for determining undetermined coefficients of a Gaussian function using the reflection characteristic measurement values and calculating corrected reflection characteristic values by correcting errors created by an angle of inclination $x_0$ of a normal 5n to a measurement object 5a of the measurement object 5 with respect to a center axis 2n of a colorimeter main body 2 using this Gaussian function.

The memory 163 is comprised of, e.g., a RAM, EEPROM or ROM. Measurement results and the like are temporarily saved, and an operation program of the controller 160 including the measurement controller 161 and the calculator 162 and the Gaussian function expressed by above equation (3) are stored in the memory 163.

Next, the arrangement of the first to fourth light guiding devices 110 to 140 and the illuminator 150 is described.

The illuminator 150 is arranged such that its optical axis 150L coincides with a direction at 45° to the center axis 2n of the main body 2. If the positions of the first to fourth light guiding devices 110 to 140 are expressed by angles from a reference direction 150S which is a direction symmetrical with the optical axis 150L of the illuminator 150 with respect to the center axis 2n of the main body 2 assuming that a side where the center axis 2n is located is a positive side, the first to fourth light guiding devices 110 to 140 are arranged such that their optical axes 110L, 120L. 130L, 140L coincide with directions of +15°, −15°, +45°, +110°, respectively. Accordingly, the center axis 2n and the optical axis 130L coincide with each other.

By taking the above construction, the reflected light $r_1$, $r_2$, $r_3$, $r_4$ from the measurement object 5 incident on the respective light guiding devices 110, 120, 130, 140 are successively incident on the splitter 52 by moving the movable fiber 171 of the beam switcher 170 while the light source 151 is on. Measurement results thus obtained are corrected as in the first embodiment using the Gaussian function.

The same action and effect as the first embodiment can be obtained even in the third embodiment in which the reflected light from the measurement object illuminated in one direction are detected in a multitude of directions.

The present invention is not limited to the first to third embodiments, and may be embodied as follows.

(1) Although the four illuminator, i.e., the first to fourth illuminators are provided in the first embodiment and the four light guiding devices, i.e., the first to fourth light guiding devices are provided in the third embodiment, five or more illuminators or five or more light guiding devices may be provided according to the present invention. In such cases, the four undetermined coefficients of the Gaussian function $R_g(x)$ defined by equation (3) may be determined using reflection characteristic measurement values given by the five or more illuminators or five or more light guiding devices.

(2) Although the second illuminator 20 is arranged in such a position that its optical axis 20L is symmetrical with the optical axis 10L of the first illuminator 10 with respect to the reference direction 50S in the first embodiment, the present invention is not limited thereto. The second illuminator 20 may be arranged in any desired position. In such a case, the center angle $x_0$ of the Gaussian function can be precisely calculated by arranging the second illuminator on the opposite side of the first illuminator 10 with respect to the reference direction 50S.

Similarly, although the second light guiding device 120 is arranged in such a position that its optical axis 120L is symmetrical with the optical axis 110L of the first light guiding device 110 with respect to the reference direction 150S in the third embodiment, the present invention is not limited thereto. The second light guiding device 120 may be arranged in any desired position. In such a case, the center angle $x_0$ of the Gaussian function can be precisely calculated by arranging the second light guiding device on the opposite side of the first light guiding device 110 with respect to the reference direction 150S.

(3) As described with reference to FIG. 16, errors are created in the reflection characteristic measurement values $R(x_1)$, $R(x_2)$ in the highlight direction by being particularly largely influenced by the angle of inclination $x_0$ between the object surface 5a and the main body 2. However, since the angles $x_1$, $x_2$ are located substantially symmetrically with respect to the center of the angle distribution. Directions of the errors are reverse, i.e., arrows corresponding to the correction amounts $dR_g(x_1)$ and $dR_g(x_2)$ shown in FIG. 4 are reverse.

Accordingly, in the first embodiment, an average value of corrected reflection characteristic values $R(x_1)+dR_g(x_1)$ and $R(x_2)+dR_g(x_2)$ i.e., $[R(x_1)+dR_g(x_1)+R(x_2)+dR_g(x_2)]/2$ may be considered as the angle $x_1$, i.e., the corrected reflection characteristic value in the highlight direction. In this way, the errors caused by the inclination can be canceled in a range where the angle of inclination is small, with the result that measurement precision can be further improved. The same also applies to the third embodiment.

(4) Although the function P(t) representing the distribution of the orientations of the bright materials and the reflection characteristic R(x) based on the function P(t) are approximated by the Gaussian functions in the first embodiment, the present invention is not limited thereto. For instance, they may be approximated by other symmetrical exponential functions as defined in following equation (4):

$$R_g(x)=R_0 \cdot \exp[-|(x-x_0)/d|^n]+b \quad (4)$$

wherein n is a constant larger than 0.

Particularly, since a reflectance of the bright materials depends on an incident angle in the pearl-color coating accompanied by interference, the function P(t) may deviate from a Gaussian distribution. However, equation (4) can be made into a satisfactory approximate function by giving a suitable value to n. This can also apply to the third embodiment.

(5) Although the inclination of the main body 2 is considered along a measurement plane including the optical axes 10L to 40L and 50L, it may be, in reality, considered with respect to a direction normal to such a measurement plane.

Figure 8:
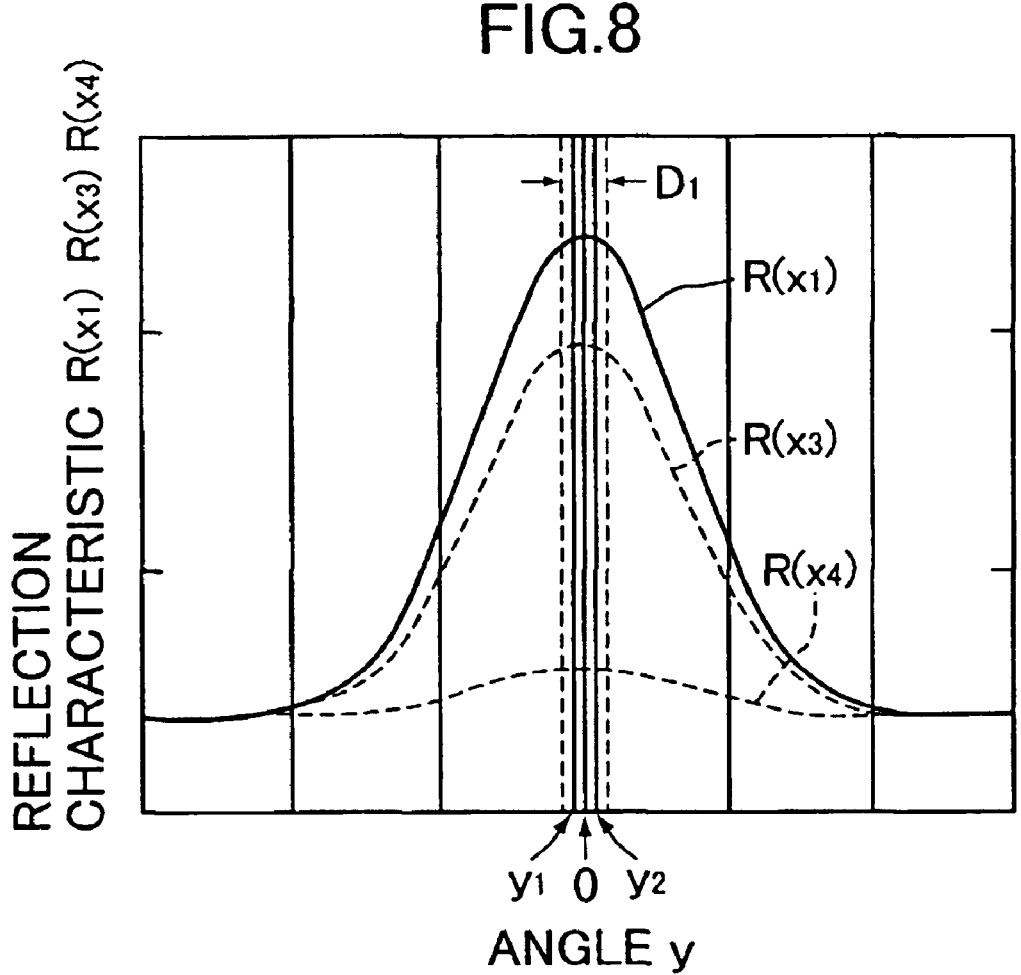
FIG. 8 is a graph showing distributions of reflection characteristic measurement values $R(x_1)$, $R(x_3)$, $R(x_4)$ by first, third and fourth illuminator at an angle of inclination y when the main body is inclined in a direction normal to the plane of FIG. 1.

In the case of such an inclination, the reflection characteristic measurement values $R(x_1)$, $R(x_3)$, $R(x_4)$ by the first, third and fourth illuminators 10, 30, 40 at the angle of inclination y are distributed as shown in FIG. 8. In other words, in FIG. 8, the values at y=0 correspond to values at $x=x_1$, $x_2$, $x_3$, $x_4$ of FIG. 4.

As is clear from FIG. 8, the reflection characteristic changes to a small degree as the angle of inclination changes at and near the center of the Gaussian function. Thus, errors resulting from the inclination in this direction are not very large. However, if the function to which the reflection characteristic is approximated is not a Gaussian function, but a function defined, for example, by equation (4), the change in the reflection characteristic in relation to the change in the angle of inclination in this direction is not negligible particularly if n is small. Accordingly, this modification is designed to reduce errors resulting from the inclination in this direction.

Figure 9:
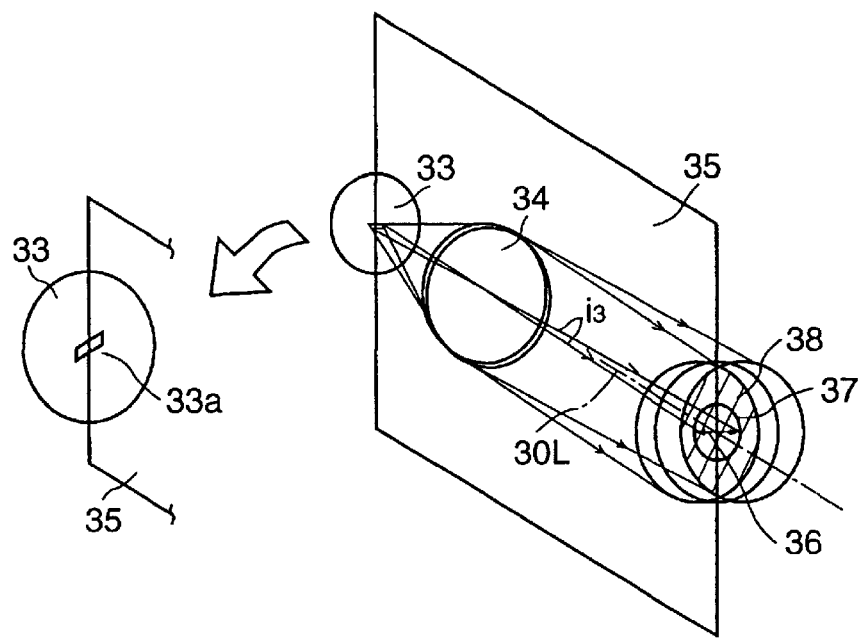
FIG. 9 is a construction diagram showing a modification of the third illuminator.

FIG. 9 is a construction diagram showing a modification of the third illuminator 30. The same parts as those in FIG. 1 are identified by the same reference numerals and the light source 31 is not shown. In FIG. 9, a measurement plane 35 is the one (corresponding to the plane of FIG. 1) including the optical axes 30L and 50L in FIG. 1, and is normal to a beam restricting plate 33.

In this modification, an opening 33a of the beam restricting plate 33 is in the form of a slit whose sides parallel to the measurement plane 35 are shorter and whose sides normal to the measurement plane 35 are longer, i.e., whose longitudinal direction is normal to the measurement plane 35. Thus, a parallel beam $i_3$ for illuminating an object surface has a width 36 in this direction in a plane normal to the measurement plane 35 as shown in FIG. 9. This width 36 corresponds to a width $D_1$ in FIG. 8. If the angle of inclination is small, a beam which gives a peak of the reflection characteristic is thought to lie in this range. Accordingly, if a light receiving range 37 of a light detector 50 lies within a common illumination area 38 of the parallel illumination beams in the range having the width 36, the inclination in the range defined by the width $D_1$ in FIG. 8 hardly influences an amount of light incident on the light detector 50.

As described above, according to this modification, errors created by the inclination of the main body 2 in the direction normal to the plane of FIG. 1, i.e., the measurement plane including the optical axes 10L to 40L and the optical axis 50L can be reduced by forming the opening 33a of the beam restrictor 33 into a rectangular shape whose sides parallel to the measurement plane 35 are shorter and whose sides perpendicular to the measurement plane 35.

Although only the third illuminator 30 is described here, the same applies to the openings 13a, 23a, 43a of the beam restricting plates 13, 23, 43 of the first, second and fourth illuminators 10, 20, 40. The same also applies to the opening 153a of the beam restricting plate 153 of the illuminator 150 according to the third embodiment. This enables reduction of errors created by the inclination of the main body 2 in the direction normal to the plane of FIG. 7 (i.e., the measurement plane including the optical axes 110L to 140L and the optical axis 150L).

Figure 10:
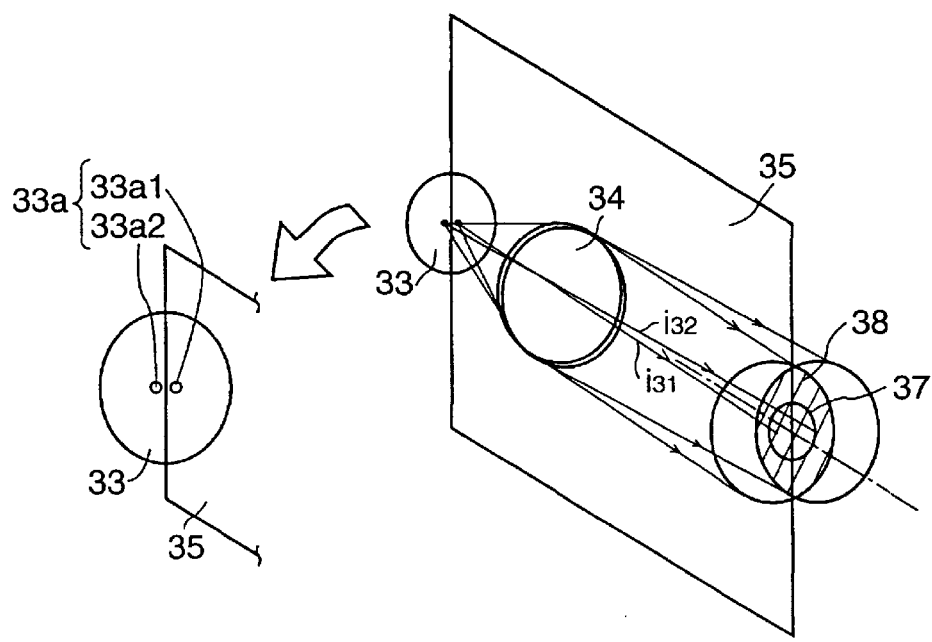
FIG. 10 is a construction diagram showing another modification of the third illuminator.

(6) Similar to the modification (5), this modification is designed to reduce errors created by the inclination of the main body 2 in the direction normal to the plane of FIG. 1, i.e., the measurement plane including the optical axes 10L to 40L and the optical axis 50L. FIG. 10 is a construction diagram showing a different modification of the third illuminator 30. The same parts as those in FIG. 9 are identified by the same reference numerals, and the light source 31 is not shown.

In this modification, a beam restricting plate 33 has two openings 33a1, 33a2 formed in symmetrical positions with respect to the optical axis 30L (measurement plane 35). Parallel beams $i_{31}$, $i_{32}$ from the openings 33a1, 3a2 are incident on a measurement object. Illumination by these parallel beams $i_{31}$, $i_{32}$ corresponds to angles $Y_1$, $Y_2$ deviated from y=0 in FIG. 8.

Here, if a colorimeter main body 2 is inclined by a very small angle in the direction normal to the plane of FIG. 1, i.e., the measurement plane including the optical axes 10L to 40L and the optical axis 50L, reflected light of the parallel beam having passed through one of the openings 33a1, 33a2 increases while a reflected light of the parallel beam having passed through the other thereof decreases so long as a light detecting range 37 of a light detector 50 lies in an illumination area 38 common to the openings 33a1, 33a2. Thus, a total intensity of the reflected light incident on the light detector 50 barely changes.

Therefore, according to this modification, errors created by the inclination of the main body 2 in the direction normal to the plane of FIG. 1 (i.e., the measurement plane including the optical axes 10L to 40L and the optical axis 50L) can be reduced by forming the two openings 33a1, 33a2 in the symmetrical positions of the beam restricting plate 33 with respect to the optical axis 30L (measurement plane 35) and setting a spacing between the openings 33a1, 33a2 such that the light detecting range 37 of the light detector 50 lies in the illumination area 38 common to the openings 33a1, 33a2.

Although only the third illuminator 30 is described here, the same applies the openings 13a, 23a, 43a of the beam restricting plates 13, 23, 43 of the first, second and fourth illuminators 10, 20, 40. The same also applies to the opening 153a of the beam restricting plate 153 of the illuminator 150 according to the third embodiment. This enables reduction of errors created by the inclination of the main body 2 in the direction normal to the plane of FIG. 7 (i.e., the measurement plane including the optical axes 110L to 140L and the optical axis 150L).

(7) Since there is a very small contribution of the reflected light from the bright materials to the reflection characteristic measurement value $R(x_4)$ obtained by the fourth illuminator 40 provided in the shade direction as described in the first embodiment, $R(x_4)$=b (offset component by the diffused reflection) can be set by ignoring such a small contribution. In such a case, the remaining three undetermined coefficients may be calculated by the least squares method. According to this modification, since the undetermined coefficients are reduced to three, the time for calculating the undetermined coefficients can be shortened and the precision can be improved as compared to the foregoing embodiments. The same applies to the reflection characteristic measurement value $R(x_4)$ obtained by the fourth light detector 140 of the third embodiment.

Figure 11:
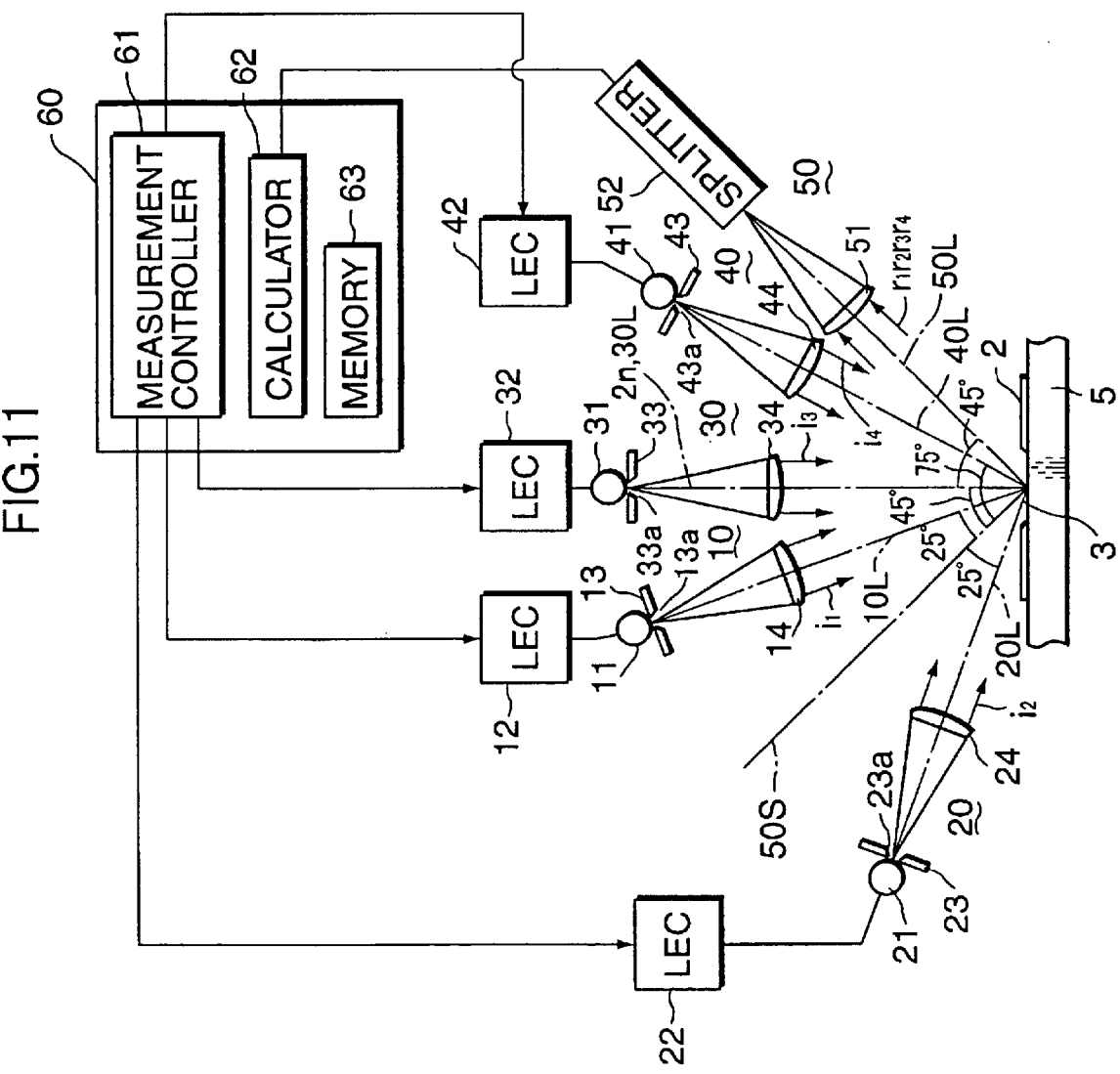
FIG. 11 is a diagram showing a modification of the multi-angle colorimeter shown in FIG. 1 in which the arrangement of the illuminator is different.

(8) The arrangement of the first to fourth illuminators 10 to 40 is not limited to those of the first and second embodiments. FIG. 11 is a diagram showing a modification of the multi-angle colorimeter of the same type of FIG. 1, in which the arrangement of the illuminator is different from that of FIG. 1. In FIG. 11, if the positions of first to fourth illuminator 10 to 40 are expressed by angles from a reference direction 50S which is a direction symmetrical with an optical axis 50L of a light detector 50 with respect to a center axis 2n of a colorimeter main body 2 assuming that a side where the center axis 2n is located is a positive side, the first to fourth illuminators 10 to 40 are arranged such that their optical axes 10L, 20L, 30L, 40L coincide with directions of +25°, −25°, +45°, +75°, respectively. The modification can also have the same operation and effects as the first and second embodiments.

Figure 12:
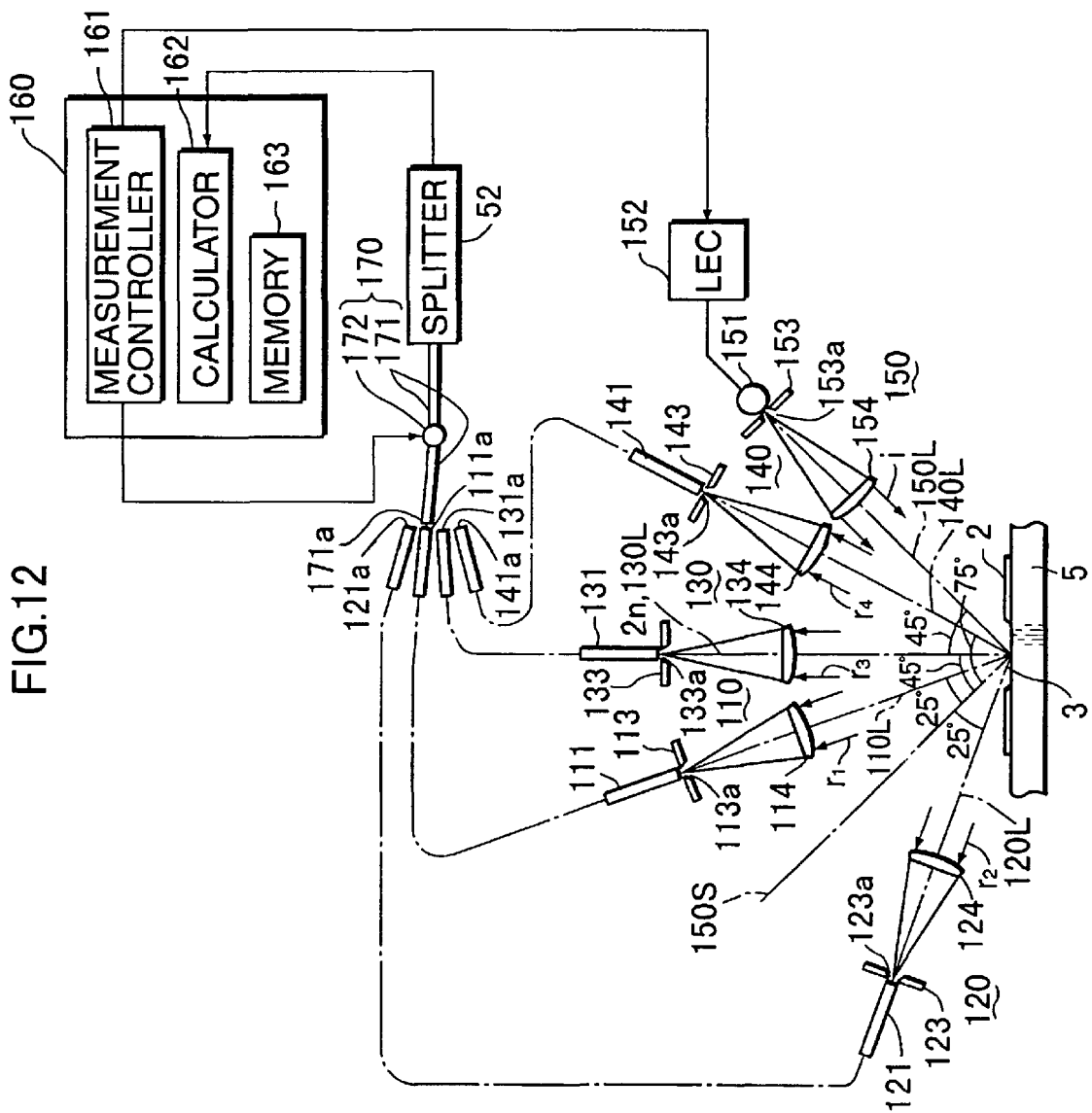
FIG. 12 is a diagram showing a modification of the multi-angle colorimeter shown in FIG. 7 in which the arrangement of the illuminator is different.

(9) The arrangement of the first to fourth light guiding devices 110 to 140 are not limited to that of the third embodiment. FIG. 12 is a diagram showing a modification of the multi-angle colorimeter of the same type of FIG. 7, in which the arrangement of the light guiding devices is different from that of FIG. 7. In FIG. 12, if the positions of first to fourth light guiding devices 110 to 140 are expressed by angles from a reference direction 50S which is a direction symmetrical with an optical axis 50L of a light detector 50 with respect to a center axis 2n of a calorimeter main body 2 assuming that a side where the center axis 2n is located is a positive side, the first to fourth light-guiding devices 10 to 140 are arranged such that their optical axes 10L, 20L. 30L. 40L coincide with directions of +25°, −25°, +45°, +75°, respectively. The modification can also have the same operation and effects as the third embodiment.

(10) Reflection characteristic values may be calculated in the arrangement of the illuminator as in the modification (8) which is different from that of FIG. 1 using the Gaussian function obtained in the first embodiment. In such a case, the calculator 62 sets x1=25° in $R_g(x_1+x_0)$ after obtaining a Gaussian function $R_g(x)$, for example, as shown in FIG. 3. Similarly, reflection characteristic values may be calculated in the arrangement of the light detector as in the modification (9) which is different from that of FIG. 7 using the Gaussian function obtained in the third embodiment. According to this modification, the reflection characteristic values in the constructions in which the arrangement of the illuminator or the light detector is different can be estimated.

(11) Although the first and second illuminators 10, 20 are constructed by the common light source 11 in the second embodiment, the same construction as the first embodiment in which the first and second illuminators 10, 20 are individually provided with the light sources 11, 12 may be adopted as shown in FIG. 1. In this case, the same operation as the second embodiment is attained if the light emitting circuits 12, 22 are simultaneously driven by the measurement controller 61. If the light emitting circuits 12, 22 are individually driven, the reflected light $r_1$, $r_2$ are detected by the light detector 50, and the calculator 63 may add measurement values $R_1$, $R_2$ after calculating them.

(12) In the foregoing embodiments, the present invention is described with reference to a colorimeter for measuring a color of an object. However, the present invention may be applied to other measuring apparatus such as a glossimeter for measuring a gloss, and a densitometer for measuring a concentration.

As described above, a first inventive color measuring apparatus comprises: a main body having an opening opposed to an object to be measured; a plurality of illuminators for illuminating a surface of the object in directions different from one another; a light detector for detecting reflected light in a specified direction from the object illuminated by the plurality of illuminators and outputting light detection signals corresponding to light intensities; a first calculator for calculating reflection characteristic measurement values of the measurement object in correspondence with the plurality of illuminators based on the light detection signals; a storage device for storing an approximate function having an angle of an illuminating direction with respect to a reference direction as a variable if the reference direction is a direction symmetrical with the specific direction with respect to a center axis of the main body in parallel to a normal to the opening, and having a plurality of undetermined coefficients including an angle of inclination of the center axis of the main body with respect to a normal to the surface of the object; and a second calculator for determining a plurality of undetermined coefficients based on the respective reflection characteristic measurement values and the angles of the illuminating directions, and correcting the respective reflection characteristic measurement values using the approximate function whose undetermined coefficients are determined.

With this construction, the surface of the measurement object is illuminated by the plurality of illuminators in the different directions, the reflected light in the specific direction from the illuminated measurement object are detected by the light detector, the light detection signals corresponding to the light intensities are outputted, and the first calculator calculates the reflection characteristic measurement values of the measurement object in correspondence with the plurality of illuminators based on the light detection signals.

The approximate function having the angle of illuminating direction with respect to the reference direction as a variable if the reference direction is a direction symmetrical with the specific direction with respect to the center axis of the main body in parallel to the normal to the measurement opening, and having the plurality of undetermined coefficients including the angle of inclination of the center axis of the main body with respect to the normal to the surface of the measurement object is stored in the storage device.

The second calculator determines the plurality of undetermined coefficients such that the values obtained by substituting the angles of the illuminating directions of the respective illuminators into the approximate function are maximally approximated to the respective reflection characteristic measurement values, and the reflection characteristic measurement values corresponding to the plurality of illuminators are corrected using the approximate function whose undetermined coefficients are determined. Accordingly, errors created by the angle of inclination of the center axis of the main body with respect to the normal to the surface of the measurement object can be reduced, thereby improving the measurement precision.

The approximate function may be preferably a symmetrical function having a maximum value at a specified angle deviated from the reference direction by the angle of inclination of the center axis of the main body with respect to the normal to the object surface.

With such an approximate function, in the case that the measurement object is something having a metallic coating or pearl-color coating in which bright materials comprised of thin pieces of aluminum or mica are contained in a film, the reflection characteristic values in relation to the angles of the illuminating directions of the respective illuminators are located on a substantially symmetrical curve having a maximum value at the specified angle deviated from the reference direction by the angle of inclination of the center axis of the main body with respect to the normal to the surface of the measurement object. The reflection characteristic can be more precisely approximated by using the approximate function which is symmetrical with respect to its maximum value at the specified angle. Therefore, errors created by the angle of inclination of the center axis of the main body with respect to the normal to the surface of the measurement object can be reduced, thereby improving a measurement precision.

It may be further preferable that the approximate function is a Gaussian function. With such an approximate function, in the case that the measurement object is something having a metallic coating or pearl-color coating, the reflection characteristic values in relation to the angles of the illuminating directions of the respective illuminators are located on a curve approximate to a normal distribution having a peak at the specified angle. The reflection characteristic can be even more precisely approximated by using the Gaussian function having a maximum value at the specified angle as the approximate function. Therefore, errors created by the above angle of inclination can be reduced, thereby further improving the measurement precision.

The approximate function may be preferably have a specified number of undetermined coefficients. In this case, the plurality of illuminators include at least the specified number of illuminators.

With this construction, since the approximate function has the specified number of undetermined coefficients and there are at least the specified number of illuminators, the specified number of undetermined coefficients of the approximate function can be securely determined such that the values obtained by substituting the angles of the illuminating directions of the respective illuminators into the approximate function are maximally approximated to the reflection characteristic measurement values of the measurement object corresponding to the respective illuminators. Therefore, the reflection characteristic measurement values corresponding to the plurality of illuminators can be corrected using the approximate function.

The plurality of illuminators may be preferably include a first illuminator provided at one side of the reference direction where the center axis of the main body is located and a second illuminator provided on the other side of the reference direction.

With this construction, in the case that the measurement object is something having a metallic coating or pearl-color coating in which bright materials comprised of thin pieces of aluminum or mica are contained in a film, the reflection characteristic values in relation to the angles of the illuminating directions of the respective illuminators are located on a substantially symmetrical curve having a maximum value at the specified angle deviated from the reference direction by the angle of inclination of the center axis of the main body with respect to the normal to the surface of the measurement object. By providing the first illuminator at one side of the reference direction where the center axis of the main body is located and the second illuminator at the other side of the reference direction, a condition that the specified angle is located between the angle of the illuminating direction of the first illuminator and the angle of the illuminating direction of the second illuminator can be set. Accordingly, the undetermined coefficient of the approximate function corresponding to the angle of inclination can be more precisely determined. Thus, errors created by this angle of inclination can be reduced, thereby further improving the measurement precision.

The first and second illuminators may be preferably provided in positions symmetrical with each other with respect to the reference direction. With this construction, the undetermined coefficient of the approximate function corresponding to the angle of inclination can be more precisely determined since the first and second illuminators are provided in positions symmetrical with each other with respect to the reference direction. Thus, errors created by this angle of inclination can be reduced, thereby further improving the measurement precision.

A second inventive measurement apparatus comprises: a main body having an opening opposed to an object to be measured; a plurality of illuminators for illuminating a surface of the object in directions different from one another, the plurality of illuminators including: a first illuminator provided at one side of a reference direction where a center axis of the main body is located and a second illuminator provided on the other side of the reference direction if the reference direction is a direction symmetrical with the specific direction with respect to the center axis of the main body in parallel to a normal to the opening, the first and second illuminators being provided in positions symmetrical with each other with respect to the reference direction; a light detector for detecting reflected light in a specified direction from the object illuminated by the plurality of illuminators and outputting light detection signals corresponding to light intensities; and a calculator for calculating a reflection characteristic of the object corresponding to the first illuminator based on a sum of the light detection signals corresponding to the first and second illuminator.

With this construction, the surface of the measurement object is illuminated by the plurality of illuminators in the different directions, and the reflected light in the specified direction from the illuminated measurement object are detected by the light detector, which in turn outputs the light detection signals corresponding to the intensities of the detected lights. Since the first and second illuminator are provided in the positions symmetrical with each other with respect to the reference direction, the intensity of the reflected light corresponding to one of the first and second illuminator increases while that of the reflected light corresponding to the other thereof decreases if the center axis of the main body is inclined with respect to the normal to the object surface. Accordingly, the sum of the light detection signals corresponding to the first and second illuminator is substantially constant regardless of whether or not the center axis of the main body is inclined with respect to the normal to the object surface and a degree of inclination. Thus, the reflection characteristic of the measurement object corresponding to the first illuminator can be precisely calculated based on the sum of the light detection signals corresponding to the first and second illuminator.

In the case that an angle between the illuminating direction of the first illuminator and the reference direction is small, the inclination of the center axis of the main body with respect to the normal to the object surface largely influences the light detection signal corresponding to the first illuminator. Even in such a case, the reflection characteristic can be highly precisely measured since the sum of the light detection signals corresponding to the first and second illuminator is substantially constant.

The first and second illuminators may be simultaneously driven to illuminate the object. With this construction, since the reflected light corresponding to the first and second illuminator are simultaneously detected by the light detector, the reflection characteristic of the measurement object corresponding to the first illuminator can be directly obtained, thereby shortening a measurement time.

The first and second illuminator may be provided with a common light source shared thereby. With this construction, the measurement object is simultaneously illuminated by the first and second illuminator only by driving the common light source. Thus, the constructions of the light source and its driver can be simplified.

In the first and second inventive measurement apparatus, each of the plurality of illuminators may be include: a light source; a beam restricting plate having an opening through which a beam from the light source passes; a collimator lens for converging the beam having passed through the opening, the opening being located in vicinity of a focusing position of the collimator lens and having a rectangular shape whose sides parallel to a measurement plane including an optical axis of the light detector and optical axes of the plurality of illuminators are shorter and whose sides perpendicular to the measurement plane are longer.

With this construction, since the opening of the beam restricting plate has a rectangular shape whose sides parallel to the measurement plane including the optical axis of the light detector and the optical axes of the plurality of illuminators are shorter and whose sides perpendicular to the measurement plane are longer, the beam corresponding to little inclination passes through the openings in a range defined by the sides perpendicular to the measurement plane even if the center axis of the main body is inclined with respect to the normal to the object surface in a direction normal to the measurement plane. Thus, measurement errors due to the inclination of the center axis of the main body in the direction normal to the measurement plane can be reduced. In this case, the shorter the sides parallel to the measurement plane, the better the parallelism of the beam, i.e., a better measurement precision.

Also, each of the plurality of illuminators may include: a light source; a beam restricting plate having first and second openings through which a beam from the light source passes: a collimator lens for converging the beam having passed through the first and second openings, the first and second openings being located in vicinity of a focusing position of the collimator lens in positions symmetrical with each other with respect to a measurement plane including an optical axis of the light detector and optical axes of the plurality of illuminators.

With this construction, since the first and second openings of the beam restricting plate are formed in the positions symmetrical with each other with respect to the measurement plane, the beam from one of the first and second openings increases while that from the other thereof decreases only by the same amount if the center axis of the main body is inclined with respect to the normal to the object surface in the direction normal to the measurement plane. Thus, measurement errors due to the inclination of the center axis of the main body in the direction normal to the measurement plane can be reduced. In this construction, the light detector preferably has such a light detecting angle as to include both the first and second openings.

A third inventive measurement apparatus comprises: a main body having an opening opposed to an object to be measured; an illuminator for illuminating a surface of the object in a specific direction; a plurality of light detectors for detecting reflected light in directions different from one another from the object illuminated by the illuminator and outputting light detection signals corresponding to light intensities; a first calculator for calculating reflection characteristic measurement values of the object in correspondence with the plurality of light detectors based on the light detection signals; a storage device for storing an approximate function having an angle of a light detecting direction with respect to a reference direction as a variable if the reference direction is a direction symmetrical with the specific direction with respect to a center axis of the main body in parallel to a normal to the measurement opening, and having a plurality of undetermined coefficients including an angle of inclination of the center axis of the main body with respect to a normal to the surface of the object; and a second calculator for determining a plurality of undetermined coefficients based on the respective reflection characteristic measurement values and the angles of the light detecting directions, and correcting the respective reflection characteristic measurement values using the approximate function whose undetermined coefficients are determined.

With this construction, the surface of the measurement object is illuminated by the illuminator in the specified direction, the reflected light in the different directions from the illuminated measurement object are detected by the plurality of light detectors, the light detection signals corresponding to the light intensities are outputted, and the first calculator calculates the reflection characteristic measurement values of the measurement object in correspondence with the plurality of light detectors based on the light detection signals. The approximate function having the angle of the illuminating direction with respect to the reference direction as a variable if the reference direction is a direction symmetrical with the specific direction with respect to the center axis of the main body in parallel to the normal to the measurement opening, and having the plurality of undetermined coefficients including the angle of inclination of the center axis of the main body with respect to the normal to the surface of the measurement object is stored in the storage device. The second calculator determines the plurality of undetermined coefficients such that the values obtained by substituting the angles of the light detecting directions of the respective light detectors into the approximate function are maximally approximated to the respective reflection characteristic measurement values, and the reflection characteristic measurement values corresponding to the plurality of light detectors are corrected using the approximate function whose undetermined coefficients are determined. Accordingly, errors created by the angle of inclination of the center axis of the main body with respect to the normal to the surface of the measurement object can be reduced, thereby improving the measurement precision.

The approximate function may be a symmetrical function having a maximum value at a specified angle deviated from the reference direction by the angle of inclination of the center axis of the main body with respect to the normal to the object surface.

With such an approximate function, in the case that the measurement object is something having a metallic coating or pearl-color coating in which bright materials comprised of thin pieces of aluminum or mica are contained in a film, the reflection characteristic values in relation to the angles of the light detecting directions of the respective light detectors are located on a substantially symmetrical curve having a maximum value at the specified angle deviated from the reference direction by the angle of inclination of the center axis of the main body with respect to the normal to the surface of the measurement object. The reflection characteristic can be more precisely approximated by using the approximate function which is symmetrical with respect to its maximum value at the specified angle. Therefore, errors created by the angle of inclination of the center axis of the main body with respect to the normal to the surface of the measurement object can be reduced, thereby improving the measurement precision.

The approximate function may be preferably a Gaussian function. With such an approximate function, in the case that the measurement object is something having a metallic coating or pearl-color coating, the reflection characteristic values in relation to the angles of the light detecting directions of the respective light detectors are located on a curve approximate to a normal distribution having a peak at the specified angle. The reflection characteristic can be even more precisely approximated by using the Gaussian function having a maximum value at the specified angle as the approximate function. Therefore, errors created by the above angle of inclination can be reduced, thereby further improving the measurement precision.

The approximate function may preferably have a specified number of undetermined coefficients. In this case, the plurality of light detectors include at least the specified number of light detectors.

With this construction, since the approximate function has the specified number of undetermined coefficients and there are at least the specified number of light detectors, the specified number of undetermined coefficients of the approximate function can be securely determined such that the values obtained by substituting the angles of the light detecting directions of the respective light detectors into the approximate function are maximally approximated to the reflection characteristic measurement values of the measurement object corresponding to the respective light detectors. Therefore, the reflection characteristic measurement values corresponding to the plurality of light detectors can be corrected using the approximate function.

The plurality of light detectors may include a first light detector provided at one side of the reference direction where the center axis of the main body is located and a second light detector provided on the other side of the reference direction.

With this construction, in the case that the measurement object is something having a metallic coating or pearl-color coating in which bright materials comprised of thin pieces of aluminum or mica are contained in a film, the reflection characteristic values in relation to the angles of the light detecting directions of the respective light detectors are located on a substantially symmetrical curve having a maximum value at the specified angle deviated from the reference direction by the angle of inclination of the center axis of the main body with respect to the normal to the surface of the measurement object. By providing the first light detector at one side of the reference direction where the center axis of the main body is located and the second light detector at the other side of the reference direction, a condition that the specified angle is located between the angle of the light detecting direction of the first light detector and the angle of the light detecting direction of the second light detector can be set. Accordingly, the undetermined coefficient of the approximate function corresponding to the angle of inclination can be more precisely determined. Thus, errors created by this angle of inclination can be reduced, thereby further improving the measurement precision.

The first and second light detectors may be preferably provided in positions symmetrical with each other with respect to the reference direction. With this construction, the undetermined coefficient of the approximate function corresponding to the angle of inclination can be more precisely determined by providing the first and second illuminator in positions symmetrical with each other with respect to the reference direction. Thus, errors created by this angle of inclination can be reduced, thereby further improving the measurement precision.

A fourth inventive measurement apparatus comprises: a main body having an opening opposed to an object to be measured; an illuminator for illuminating a surface of the object in a specific direction; a plurality of light detectors for detecting reflected light in directions different from one another from the object illuminated by the illuminator and outputting light detection signals corresponding to light intensities. The plurality of light detectors includes: a first light detector provided at one side of a reference direction where a center axis of the main body is located and a second light detector provided on the other side of the reference direction if the reference direction is a direction symmetrical with the specific direction with respect to the center axis of the main body in parallel to a normal to the opening the first and second light detectors being provided in positions symmetrical with each other with respect to the reference direction. Further, the inventive apparatus is provided with a calculator for calculating a reflection characteristic of the object corresponding to the first light detector based on a sum of the light detection signals corresponding to the first and second light detectors.

With this construction, the surface of the measurement object is illuminated by the illuminator in the specific direction, and the reflected light in the different directions from the illuminated measurement object are detected by the light detector, which in turn outputs the light detection signals corresponding to the intensities of the detected lights. Since the first and second light detector are provided in the positions symmetrical with one another with respect to the reference direction, the intensity of the reflected light detected by one of the first and second light detector increases while that of the reflected light detected by the other thereof decreases if the center axis of the main body is inclined with respect to the normal to the object surface. Accordingly, the sum of the light detection signals outputted from the first and second light detector is substantially constant regardless of whether or not the center axis of the main body is inclined with respect to the normal to the object surface and a degree of inclination. Thus, the reflection characteristic of the measurement object corresponding to the first light detector can be precisely calculated based on the sum of the light detection signals outputted from the first and second light detectors.

In the case that an angle between the light detecting direction of the first light detector and the reference direction is small, the inclination of the center axis of the main body with respect to the normal to the object surface largely influences the light detection signal outputted from the first light detector. Even in such a case, the reflection characteristic can be highly precisely measured since the sum of the light detection signals outputted from the first and second light detector is substantially constant.

In the third and fourth inventive measurement apparatus, the illuminator may be preferably provided with: a light source; a beam restricting plate having an opening through which a beam from the light source passes; a collimator lens for converging the beam having passed through the opening, the opening being located in vicinity of a focusing position of the collimator lens and having a rectangular shape whose sides parallel to a measurement plane including optical axes of the plurality of light detectors and an optical axis of the illuminator are shorter and whose sides perpendicular to the measurement plane are longer.

With this construction, since the opening of the beam restricting plate has a rectangular shape whose sides parallel to the measurement plane including the optical axes of the plurality of the light detectors and the optical axis of the illuminator are shorter and whose sides perpendicular to the measurement plane are longer, the beam corresponding to little inclination passes through the openings in a range defined by the sides perpendicular to the measurement plane even if the center axis of the main body is inclined with respect to the normal to the object surface in a direction normal to the measurement plane. Thus, measurement errors due to the inclination of the center axis of the main body in the direction normal to the measurement plane can be reduced. In this case, the shorter the sides parallel to the measurement plane, the better the parallelism of the beam, i.e., measurement precision is improved.

In the third and fourth measurement apparatus, also, the illuminator may be preferably provided with: a light source; a beam restricting plate having first and second openings through which a beam from the light source passes; a collimator lens for converging the beam having passed through the first and second openings, the first and second openings being located in vicinity of a focusing position of the collimator lens in positions symmetrical with each other with respect to a measurement plane including optical axes of the plurality of a light detectors and an optical axis of the illuminator.

With this construction, since the first and second openings of the beam restricting plate are formed in the positions symmetrical with each other with respect to the measurement plane including the optical axes of the plurality of the light detector and the optical axis of the illuminator, the beam from one of the first and second openings increases while that from the other thereof decreases only by the same amount if the center axis of the main body is inclined with respect to the normal to the object surface in the direction normal to the measurement plane. Thus, measurement errors due to the inclination of the center axis of the main body in the direction normal to the measurement plane can be reduced. In this construction, the plurality of light detectors may preferably have such a light detecting angle as to include both the first and second openings.

The reflection characteristic may be a spectral reflection characteristic dependent on wavelength. With such a reflection characteristic, since the spectral reflection characteristic of the measurement object for each wavelength can be obtained, various reflection characteristics of the measurement object can be obtained in addition to the color of the measurement object.

In a specific construction of the inventive measurement apparatus having the plurality of illuminators including the first and second illuminators and one light detector, the light detector may be provided such that the specific direction is at +45° with respect to the center axis of the main body, and the first and second illuminators may be provided such that their optical axes are at +15° and at −15°, respectively, if the reference direction is at 0° and the side where the center axis is located is a positive side. The plurality of illuminators may also include a third illuminator whose optical axis is at +45° and a fourth illuminator whose optical axis is at +110°. Alternatively, the first and second illuminators may be provided such that their optical axes are at +25° and at −25°, respectively, if the reference direction is at 0° and the side where the center axis is located is a positive side, and the plurality of illuminators may also include a third illuminator whose optical axis is at +45° and a fourth illuminator whose optical axis is at +75°.

In the above constructions, the reflection characteristic in the so-called highlight direction is obtained by the first illuminator, the reflection characteristic in the so-called shade direction is obtained by the fourth illuminator, and an intermediate reflection characteristic is obtained by the third illuminator with the errors created by the inclination of angle of the center axis of the main body with respect to the normal to the object surface reduced. In the case that the measurement object is something having a metallic coating or pearl-color coating in which bright materials comprised of thin pieces of aluminum or mica are contained in a film, correct reflection characteristics of the measurement object can be obtained.

Further, in a specific construction of the inventive measurement apparatus having one illuminator and a plurality of light detectors including the first and second light detector, the illuminator may be provided such that the specific direction is at +45° with respect to the center axis of the main body, and the first and second light detectors may be provided such that their optical axes are at +15° and at −15°, respectively, if the reference direction is at 0° and the side where the center axis is located is a positive side. The plurality of light detectors may also include a third light detector whose optical axis is at +45° and a fourth light detector whose optical axis is at +110°. Alternatively, the first and second light detectors may be provided such that their optical axes are at +25° and at −25°, respectively, if the reference direction is at 0° and the side where the center axis is located is a positive side, and the plurality of light detectors may also include a third light detector whose optical axis is at +45° and a fourth light detector whose optical axis is at +75°.

In the above constructions, the reflection characteristic in the highlight direction is obtained by the first light detector, the reflection characteristic in the shade direction is obtained by the fourth light detector, and the intermediate reflection characteristic is obtained by the third light detector with the errors created by the inclination of angle of the center axis of the main body with respect to the normal to the object surface reduced. In the case that the measurement object is something having a metallic coating or pearl-color coating in which bright materials comprised of thin pieces of aluminum or mica are contained in a film, correct reflection characteristics of the measurement object can be obtained.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds are therefore intended to embraced by the claims.

What is claimed is:

1. A measurement apparatus for measuring color of an object, comprising:
    a main body having an opening opposed to an object to be measured;
    a plurality of illuminators for illuminating a surface of the object in directions different from one another;
    a light detector for detecting reflected light in a specified direction from the object illuminated by the plurality of illuminators and outputting light detection signals corresponding to light intensities;
    a first calculator for calculating reflection characteristic measurement values of the measurement object in correspondence with the plurality of illuminators based on the light detection signals;
    a storage device for storing an approximate function having an angle of an illuminating direction with respect to a reference direction as a variable in a condition that a direction symmetrical with the specified direction with respect to a center axis of the main body in parallel to a normal to the opening is defined as the reference direction, and having a plurality of undetermined coefficients including an angle of inclination of the center axis of the main body with respect to a normal to the surface of the object; and
    a second calculator for determining the plurality of undetermined coefficients based on the respective reflection characteristic measurement values and the angles of the illuminating directions, and correcting the respective reflection characteristic measurement values using the approximate function whose undetermined coefficients are determined.

2. A measurement apparatus according to claim 1, wherein the approximate function is a symmetrical function having a maximum value at a specified angle deviated from the reference direction by the angle of inclination of the center axis of the main body with respect to the normal to the object surface.

3. A measurement apparatus according to claim 2, wherein the approximate function is a Gaussian function.

4. A measurement apparatus according to claim 2, wherein the approximate function has a specified number of undetermined coefficients, and the plurality of illuminators include at least the specified number of illuminators.

5. A measurement apparatus according to claim 2, wherein the plurality of illuminators include a first illuminator provided at one side of the reference direction where the center axis of the main body is located and a second illuminator provided on the other side of the reference direction.

6. A measurement apparatus according to claim 5, wherein the first and second illuminators are provided in positions symmetrical with each other with respect to the reference direction.

7. A measurement apparatus according to claim 1, wherein each of the plurality of illuminators includes
    a light source;
    a beam restricting plate having an opening through which a beam from the light source passes;
    a collimator lens for converging the beam having passed through the opening, the opening being located in vicinity of a focusing position of the collimator lens and having a rectangular shape whose sides parallel to a measurement plane including an optical axis of the light detector and optical axes of the plurality of illuminators are shorter and whose sides perpendicular to the measurement plane are longer.

8. A measurement apparatus according to claim 1, wherein each of the plurality of illuminators includes
    a light source;
    a beam restricting plate having a first and second openings through which a beam from the light source passes;
    a collimator lens for converging the beam having passed through the first and second openings, the first and second openings being located in vicinity of a focusing position of the collimator lens in positions symmetrical with each other with respect to a measurement plane including an optical axis of the light detector and optical taxes of the plurality of illuminators.

9. A measurement apparatus according to claim 1, wherein the reflection characteristic is a spectral reflection characteristic dependent on wavelength.

10. A measurement apparatus for measuring color of an object, comprising:
    a main body having an opening opposed to an object to be measured;
    a plurality of illuminators for illuminating a surface of the object in directions different from one another, the plurality of illuminators including:

a first illuminator provided at one side of a reference direction where a center axis of the main body is located, and a second illuminator provided on the other side of the reference direction, in a condition that a direction symmetrical with a specified direction with respect to a center axis of the main body in parallel to a normal to the opening is defined as the reference direction, the first and second illuminators being provided in positions symmetrical with each other with respect to the reference direction;

a light detector for detecting reflected light in the specified direction from the object illuminated by the plurality of illuminators and outputting light detection signals corresponding to light intensities; and a calculator for calculating a reflection characteristic of the object corresponding to the first illuminator based on a sum of the light detection signals corresponding to the first and second illuminator.

11. A measurement apparatus according to claim 10, wherein the first and second illuminators simultaneously illuminate the object.

12. A measurement apparatus according to claim 11, wherein the first and second illuminator are provided with a common light source shared thereby.

13. A measurement apparatus according to claim 10, wherein each of the plurality of illuminators includes a light source;

a beam restricting plate having an opening through which a beam from the light source passes;

a collimator lens for converging the beam having passed through the opening, the opening being located in vicinity of a focusing position of the collimator lens and having a rectangular shape whose sides parallel to a measurement plane including an optical axis of the light detector and optical axes of the plurality of illuminators are shorter and whose sides perpendicular to the measurement plane are longer.

14. A measurement apparatus according to claim 10, wherein each of the plurality of illuminators includes a light source;

a beam restricting plate having a first and second openings through which a beam from the light source passes;

a collimator lens for converging the beam having passed through the first and second openings, the first and second openings being located in vicinity of a focusing position of the collimator lens in positions symmetrical with each other with respect to a measurement plane including an optical axis of the light detector and optical axes of the plurality of illuminators.

15. A measurement apparatus according to claim 10, wherein the reflection characteristic is a spectral reflection characteristic dependent on wavelength.

16. A measurement apparatus for measuring color of an object, comprising:

a main body having an opening opposed to an object to be measured;

an illuminator for illuminating a surface of the object in a specified direction;

a plurality of light detectors for detecting reflected light in directions different from one another from the object illuminated by the illuminator and outputting light detection signals corresponding to light intensities;

a first calculator for calculating reflection characteristic measurement values of the object in correspondence with the plurality of light detectors based on the light detection signals;

a storage device for storing an approximate function having an angle of a light detecting direction with respect to a reference direction as a variable in a condition that a direction symmetrical with the specified direction with respect to a center axis of the main body in parallel to a normal to the measurement opening is defined as the reference direction, and having a plurality of undetermined coefficients including an angle of inclination of the center axis of the main body with respect to a normal to the surface of the object; and a second calculator for determining the plurality of undetermined coefficients based on the respective reflection characteristic measurement values and the angles of the light detecting directions, and correcting the respective reflection characteristic measurement values using the approximate function whose undetermined coefficients are determined.

17. A measurement apparatus according to claim 16, wherein the approximate function is a symmetrical function having a maximum value at a specified angle deviated from the reference direction by the angle of inclination of the center axis of the main body with respect to the normal to the object surface.

18. A measurement apparatus according to claim 17, wherein the approximate function is a Gaussian function.

19. A measurement apparatus according to claim 17, wherein the approximate function has a specified number of undetermined coefficients, and the plurality of light detectors include at least the specified number of light detectors.

20. A measurement apparatus according to claim 17, wherein the plurality of light detectors include a first light detector provided at one side of the reference direction where the center axis of the main body is located and a second light detector provided on the other side of the reference direction.

21. A measurement apparatus according to claim 20, wherein the first and second light detectors are provided in positions symmetrical with each other with respect to the reference direction.

22. A measurement apparatus according to claim 16, wherein the illuminator includes:

a light source;

a beam restricting plate having an opening through which a beam from the light source passes;

a collimator lens for converging the beam having passed through the opening, the opening being located in vicinity of a focusing position of the collimator lens and having a rectangular shape whose sides parallel to a measurement plane including optical axes of the plurality of light detectors and an optical axis of the illuminator are shorter and whose sides perpendicular to the measurement plane are longer.

23. A measurement apparatus according to claim 16, wherein the illuminator includes:

a light source;

a beam restricting plate having a first and second openings through which a beam from the light source passes;

a collimator lens for converging the beam having passed through the first and second openings, the first and second openings being located in vicinity of a focusing position of the collimator lens in positions symmetrical with each other with respect to a measurement plane including optical axes of the plurality of light detectors and an optical axis of the illuminator.

24. A measurement apparatus according to claim 16, wherein the reflection characteristic is a spectral reflection characteristic dependent on wavelength.

25. A measurement apparatus for measuring color of an object, comprising:

a main body having an opening opposed to an object to be measured;

an illuminator for illuminating a surface of the object in a specified direction;

a plurality of light detectors for detecting reflected light in directions different from one another from the object illuminated by the illuminator and outputting light detection signals corresponding to light intensities, the plurality of light detectors including:

a first light detector provided at one side of a reference direction where a center axis of the main body is located, and a second light detector provided on the other side of the reference direction, in a condition that a direction symmetrical with the specified direction with respect to the center axis of the main body in parallel to a normal to the opening is defined as the reference direction, the first and second light detectors being provided in positions symmetrical with each other with respect to the reference direction;

a calculator for calculating a reflection characteristic of the object corresponding to the first light detector based on a sum of the light detection signals corresponding to the first and second light detectors.

26. A measurement apparatus according to claim 25, wherein the illuminator includes:

a light source;

a beam restricting plate having an opening through which a beam from the light source passes;

a collimator lens for converging the beam having passed through the opening, the opening being located in vicinity of a focusing position of the collimator lens and having a rectangular shape whose sides parallel to a measurement plane including optical axes of the plurality of light detectors and an optical axis of the illuminator are shorter and whose sides perpendicular to the measurement plane are longer.

27. A measurement apparatus according to claim 25, wherein the illuminator includes:

a light source;

a beam restricting plate having a first and second openings through which a beam from the light source passes;

a collimator lens for converging the beam having passed through the first and second openings, the first and second openings being located in vicinity of a focusing position of the collimator lens in positions symmetrical with each other with respect to a measurement plane including optical axes of the plurality of light detectors and an optical axis of the illuminator.

28. A measurement apparatus according to claim 25, wherein the reflection characteristic is a spectral reflection characteristic dependent on wavelength.

* * * * *